(12) United States Patent
Glaser

(10) Patent No.: US 7,462,485 B2
(45) Date of Patent: Dec. 9, 2008

(54) MODIFIED ERYTHROCYTES AND USES THEREOF

(76) Inventor: Lawrence F. Glaser, 10705 Averett Dr., Fairfax Station, VA (US) 22039

( * ) Notice: Subject to any disclaimer, the term of this patent is extended or adjusted under 35 U.S.C. 154(b) by 337 days.

(21) Appl. No.: 11/245,074

(22) Filed: Oct. 7, 2005

(65) Prior Publication Data
US 2007/0082392 A1    Apr. 12, 2007

(51) Int. Cl.
*C12N 15/85* (2006.01)
(52) U.S. Cl. ..................................... 435/372
(58) Field of Classification Search .................. None
See application file for complete search history.

(56) References Cited

U.S. PATENT DOCUMENTS

| | | | |
|---|---|---|---|
| 4,356,172 A | 10/1982 | Nakao et al. | |
| 5,061,620 A | 10/1991 | Tsukamoto et al. | |
| 5,236,835 A | 8/1993 | Mouneimne et al. | |
| 5,612,207 A | 3/1997 | Nicolau et al. | |
| 5,763,197 A | 6/1998 | Tsukamoto et al. | |
| 5,798,206 A | 8/1998 | Neurath et al. | |
| 6,130,207 A | 10/2000 | Dean et al. | |
| 6,147,052 A | 11/2000 | Chau | |
| 6,245,207 B1 | 6/2001 | Yasuda et al. | |
| 6,333,171 B1 | 12/2001 | Klatzmann et al. | |
| 6,361,998 B1 | 3/2002 | Bell et al. | |
| 6,482,585 B2 | 11/2002 | Dottori | |
| 6,514,758 B2 | 2/2003 | Wong | |
| 6,623,937 B2 | 9/2003 | Bonini et al. | |
| 6,656,471 B1 | 12/2003 | Sastry et al. | |
| 6,720,325 B2 | 4/2004 | Miller | |
| 6,797,462 B1 | 9/2004 | Kappes et al. | |
| 2001/0006772 A1 | 7/2001 | Goldstein et al. | |
| 2003/0207247 A1 | 11/2003 | Stassinopoulos et al. | |
| 2004/0146846 A1 | 7/2004 | Dottori | |
| 2004/0243105 A1 | 12/2004 | Swan et al. | |

OTHER PUBLICATIONS

Zeira et al., Full-length CD4 electroinserted in the erythrocyte membrane as a long-lived inhibitor of infection by human immunodeficiency virus, Proc. Natl. Acad. Sci., 1991, 88:4409-4413.*
Hannig et al., Stability and immunological reactivity of recombinant membrane CD4 electroinserted into the plasma membrane of erythrocytes, FEBS Letters, 1995, 359:9-14.*
Cournoyer et al., Gene Therapy of the Immune System, Annual review of immunology, 1993, 11:297-329.*
Lachgar et al., Biomed & Pharmacother, Binding of HIV-1 to RBCs involves the Duffy Antigen Receptors for Chemokines (DARC), 1998, 52:436-439.*
J. Anderson et al., *Retroviriology 2005*, CXCR2 and CCR5 shRNA transgenic CD34+ cell derived macrophages are functionally normal and resist HIV-1 infection, 2:53, pp. 1-11 (2005).
BBC News, 'Test tube' hope for hep C drug, (2005), pp. 1-3.

N. Cheonis, *Bulletin of Experimental Treatments for AIDS*, "Structured Treatment Interruption: Future Protocol or Wishful Thinking?", San Francisco Aids Foundation, Spring 2000, pp. 1-22.
R.J. Cherry et al., *The Journal of Cell Biology*, "Detection of Dimers of Dimers of Human Leukocyte Antigen (HLA)-DR on the Surface of Living Cells by Single-Practice Fluorescence Imaging", vol. 40, No. 1, Jan. 12, 1998 pp. 71-79.
M.P. Fache et al., *The Journal of Cell Biology*, "Endocytotic elimination and domain-selective tethering constitute a potential mechanism of protein segregation at the axonal initial segment", vol. 166, No. 4, Aug. 16, 2004, pp. 571-578.
A.M. Fonseca et al., *Blood*, Red blood cells inhibit activation-induced cell death and oxidative stress in human peripheral blood T lumphocytes, vol. 97, No. 10, May, 15, 2001, pp. 3152-3160.
T.B.H. Geijtenbeek et al., *The Journal of Biological Chemistry*, "Identification of Different Binding Sites in the Dendritic Cell-specific Receptor DC-Sign for Intercellular Adhesion Molecule 3 and HIV-1", vol. 277, No. 13, (2002), pp. 11314-11320.
W.C. Greene et al., *HIV InSite*, "Molecular Insights Into HIV Biology", Feb. 2003, pp. 1-20.
P.D. Kwong et al., *Journal of Virology*, "Oligomeric Modeling and Electrostatic Analysis of the gp120 Envelope Glycoprotein of Human Immunodeficiency Virus", vol. 74, No. 4, Feb. 2000, pp. 1961-1972.
Y. Mouneimne et al., *Biochimica et Biophysica Acta*, "Electroinsertion of full length recombinant CD4 into red blood cell membrane", 1027, (1990), pp. 53-58.
Y. Mouneimne et al., *Biochimica et Biophysica Acta*, "Electroinsertion of xeno proteins in red blood cell membranes yields a long lived protein carrier in circulation", 1066, (1991), pp. 83-89.
*NIAID Division of Aids*, "HIV Summary of Research Advances", (2002), pp. 1-4.
Project Reform, *Understanding HIV: Co-Receoptors—CCR5*, "discovery of immune cell proteins shows promise for new therapies", (2004), pp. 1-4.
U. O'Doherty et al., *Journal of Virology*, "Human Immunodeficiency Virus Type 1 Spinoculation Enhances Infection through Virus Binding", vol. 74, No. 21, Nov. 2000, pp. 10074-10080.
E.J. Platt et al., *Journal of Virology*, "Kinetic Factors Control Efficiencies of Cell Entry, Efficacies of Entry Inhibitors, and Mechanisms of Adaptation of Human Immunodeficiency Virus", vol. 79, No. 7, Apr. 2005, pp. 4347-4356.

(Continued)

*Primary Examiner*—Bruce Campbell
*Assistant Examiner*—Nicole Kinsey White

(57) ABSTRACT

The present invention provides modified erythrocytes which comprise viral receptor proteins capable of mediating entry of respective viruses into the modified erythrocytes. The present invention also provides methods of using the modified erythrocytes for the treatment or prevention of viral infections. In one embodiment, the modified erythrocytes of the present invention comprise CD4 and at least one HIV coreceptor, such as CXCR4 or CCR5. The modified erythrocytes, when administered to an HIV patient, bind to the plasma virus and induce the injection of the HIV ribonucleoprotein complex into the cells. The entrapped viral content is either degraded or deactivated within the erythrocytes, or destroyed by erythrophagocytosis.

36 Claims, No Drawings

OTHER PUBLICATIONS

S. Raffy et al., *Biophysical Journal*, "Control of Lipid Membrane Stability by Cholesterol Content", vol. 76, Apr. 1999, pp. 2072-2080.

S. Raffy et al., *The Journal of Biological Chemistry*, "Electroinsertion of Glycophorin A in Interdigitation-Fusion Giant Unilamellar Lipid Vesicles", vol. 272, No. 41, (1997), pp. 25524-25530.

A. Stromberg et al., *PNAS*, "Manipulating the genetic identity and biochemical surface properties of individual cells with electric-field-induced fusion", vol. 97, No. 1, Jan. 4, 2000, pp. 7-11.

D. Tagliasacchi et al., *Fun Science Gallery*, "Let's Observe the Blood Cells", Apr. 1997, pp. 1-17.

Helmut Dolznig et al., "Establishment of normal, terminally differentiating mouse erythroid progenitors: molecular characterization by cDNA arrays[1]", The FASEB Journal, vol. 15, Jun. 2001, pp. 1442-1444.

Alena Leroux et al., "Transcriptional and translational mechanisms of cytochrome $b_5$ reductase isoenzyme generation in humans", Biochem. J. (2001) vol. 355, pp. 529-535.

Punam Malik et al., "An In Vitro Model of Human Red Blood Cell Production From Hematopoietic Progenitor Cells",, *Blood*, vol. 91, No. 8, Apr. 15, 1998, pp. 2664-2671.

Britta Hardy et al., "Spectrin Rearrangement Early In Erythrocyte Ghost Endocytosis", J. Cell Biology, The Rockefeller Univerity Press, vol. 82, Sep. 1979, pp. 654-663.

Kiaran Kirk, "Membrane Transport in the Malaria-Infected Erythrocyte", Physiological Reviews, vol. 81, No. 2, Apr. 2001, pp. 495-537.

* cited by examiner

SEQUENCE LISTING

```
<160> NUMBER OF SEQ ID NOS: 18

<210> SEQ ID NO 1
<211> LENGTH: 458
<212> TYPE: PRT
<213> ORGANISM: Homo sapiens

<400> SEQUENCE: 1

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
```

```
                65                  70                  75                  80
Asp Ser Arg Arg Ser Leu Trp Asp Gln Gly Asn Phe Pro Leu Ile Ile
                85                  90                  95
Lys Asn Leu Lys Ile Glu Asp Ser Asp Thr Tyr Ile Cys Glu Val Glu
            100                 105                 110
Asp Gln Lys Glu Glu Val Gln Leu Leu Val Phe Gly Leu Thr Ala Asn
        115                 120                 125
Ser Asp Thr His Leu Leu Gln Gly Gln Ser Leu Thr Leu Thr Leu Glu
    130                 135                 140
Ser Pro Pro Gly Ser Ser Pro Ser Val Gln Cys Arg Ser Pro Arg Gly
145                 150                 155                 160
Lys Asn Ile Gln Gly Gly Lys Thr Leu Ser Val Ser Gln Leu Glu Leu
                165                 170                 175
Gln Asp Ser Gly Thr Trp Thr Cys Thr Val Leu Gln Asn Gln Lys Lys
            180                 185                 190
Val Glu Phe Lys Ile Asp Ile Val Val Leu Ala Phe Gln Lys Ala Ser
        195                 200                 205
Ser Ile Val Tyr Lys Lys Glu Gly Glu Gln Val Glu Phe Ser Phe Pro
    210                 215                 220
Leu Ala Phe Thr Val Glu Lys Leu Thr Gly Ser Gly Glu Leu Trp Trp
225                 230                 235                 240
Gln Ala Glu Arg Ala Ser Ser Lys Ser Trp Ile Thr Phe Asp Leu
                245                 250                 255
Lys Asn Lys Glu Val Ser Val Lys Arg Val Thr Gln Asp Pro Lys Leu
            260                 265                 270
Gln Met Gly Lys Lys Leu Pro Leu His Leu Thr Leu Pro Gln Ala Leu
        275                 280                 285
Pro Gln Tyr Ala Gly Ser Gly Asn Leu Thr Leu Ala Leu Glu Ala Lys
    290                 295                 300
Thr Gly Lys Leu His Gln Glu Val Asn Leu Val Val Met Arg Ala Thr
305                 310                 315                 320
Gln Leu Gln Lys Asn Leu Thr Cys Glu Val Trp Gly Pro Thr Ser Pro
                325                 330                 335
Lys Leu Met Leu Ser Leu Lys Leu Glu Asn Lys Glu Ala Lys Val Ser
            340                 345                 350
Lys Arg Glu Lys Ala Val Trp Val Leu Asn Pro Glu Ala Gly Met Trp
        355                 360                 365
Gln Cys Leu Leu Ser Asp Ser Gly Gln Val Leu Leu Glu Ser Asn Ile
    370                 375                 380
Lys Val Leu Pro Thr Trp Ser Thr Pro Val Gln Pro Met Ala Leu Ile
385                 390                 395                 400
Val Leu Gly Gly Val Ala Gly Leu Leu Leu Phe Ile Gly Leu Gly Ile
                405                 410                 415
Phe Phe Cys Val Arg Cys Arg His Arg Arg Gln Ala Glu Arg Met
            420                 425                 430
Ser Gln Ile Lys Arg Leu Leu Ser Glu Lys Lys Thr Cys Gln Cys Pro
        435                 440                 445
His Arg Phe Gln Lys Thr Cys Ser Pro Ile
    450                 455

<210> SEQ ID NO 2
<211> LENGTH: 352
<212> TYPE: PRT
<213> ORGANISM: Homo sapiens
```

<400> SEQUENCE: 2

```
Met Asp Tyr Gln Val Ser Ser Pro Ile Tyr Asp Ile Asn Tyr Tyr Thr
 1               5                  10                  15

Ser Glu Pro Cys Gln Lys Ile Asn Val Lys Gln Ile Ala Ala Arg Leu
             20                  25                  30

Leu Pro Pro Leu Tyr Ser Leu Val Phe Ile Phe Gly Phe Val Gly Asn
         35                  40                  45

Met Leu Val Ile Leu Ile Leu Ile Asn Cys Lys Arg Leu Lys Ser Met
 50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                 85                  90                  95

Gly Asn Thr Met Cys Gln Leu Leu Thr Gly Leu Tyr Phe Ile Gly Phe
                100                 105                 110

Phe Ser Gly Ile Phe Phe Ile Ile Leu Leu Thr Ile Asp Arg Tyr Leu
            115                 120                 125

Ala Val Val His Ala Val Phe Ala Leu Lys Ala Arg Thr Val Thr Phe
        130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
                180                 185                 190

Phe Gln Thr Leu Lys Ile Val Ile Leu Gly Leu Val Leu Pro Leu Leu
            195                 200                 205

Val Met Val Ile Cys Tyr Ser Gly Ile Leu Lys Thr Leu Leu Arg Cys
        210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
                260                 265                 270

Asn Arg Leu Asp Gln Ala Met Gln Val Thr Glu Thr Leu Gly Met Thr
            275                 280                 285

His Cys Cys Ile Asn Pro Ile Ile Tyr Ala Phe Val Gly Glu Lys Phe
        290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
                340                 345                 350
```

<210> SEQ ID NO 3
<211> LENGTH: 356
<212> TYPE: PRT
<213> ORGANISM: Homo sapiens

<400> SEQUENCE: 3

```
Met Ser Ile Pro Leu Pro Leu Leu Gln Ile Tyr Thr Ser Asp Asn Tyr
 1               5                  10                  15
```

Thr Glu Glu Met Gly Ser Gly Asp Tyr Asp Ser Met Lys Glu Pro Cys
            20                  25                  30

Phe Arg Glu Glu Asn Ala Asn Phe Asn Lys Ile Phe Leu Pro Thr Ile
            35                  40                  45

Tyr Ser Ile Ile Phe Leu Thr Gly Ile Val Gly Asn Gly Leu Val Ile
            50                  55                  60

Leu Val Met Gly Tyr Gln Lys Lys Leu Arg Ser Met Thr Asp Lys Tyr
 65                  70                  75                  80

Arg Leu His Leu Ser Val Ala Asp Leu Leu Phe Val Ile Thr Leu Pro
                85                  90                  95

Phe Trp Ala Val Asp Ala Val Ala Asn Trp Tyr Phe Gly Asn Phe Leu
               100                 105                 110

Cys Lys Ala Val His Val Ile Tyr Thr Val Asn Leu Tyr Ser Ser Val
               115                 120                 125

Leu Ile Leu Ala Phe Ile Ser Leu Asp Arg Tyr Leu Ala Ile Val His
               130                 135                 140

Ala Thr Asn Ser Gln Arg Pro Arg Lys Leu Leu Ala Glu Lys Val Val
145                 150                 155                 160

Tyr Val Gly Val Trp Ile Pro Ala Leu Leu Leu Thr Ile Pro Asp Phe
               165                 170                 175

Ile Phe Ala Asn Val Ser Glu Ala Asp Asp Arg Tyr Ile Cys Asp Arg
               180                 185                 190

Phe Tyr Pro Asn Asp Leu Trp Val Val Val Phe Gln Phe Gln His Ile
               195                 200                 205

Met Val Gly Leu Ile Leu Pro Gly Ile Val Ile Leu Ser Cys Tyr Cys
               210                 215                 220

Ile Ile Ile Ser Lys Leu Ser His Ser Lys Gly His Gln Lys Arg Lys
225                 230                 235                 240

Ala Leu Lys Thr Thr Val Ile Leu Ile Leu Ala Phe Phe Ala Cys Trp
               245                 250                 255

Leu Pro Tyr Tyr Ile Gly Ile Ser Ile Asp Ser Phe Ile Leu Leu Glu
               260                 265                 270

Ile Ile Lys Gln Gly Cys Glu Phe Glu Asn Thr Val His Lys Trp Ile
               275                 280                 285

Ser Ile Thr Glu Ala Leu Ala Phe Phe His Cys Cys Leu Asn Pro Ile
               290                 295                 300

Leu Tyr Ala Phe Leu Gly Ala Lys Phe Lys Thr Ser Ala Gln His Ala
305                 310                 315                 320

Leu Thr Ser Val Ser Arg Gly Ser Ser Leu Lys Ile Leu Ser Lys Gly
               325                 330                 335

Lys Arg Gly Gly His Ser Ser Val Ser Thr Glu Ser Glu Ser Ser Ser
               340                 345                 350

Phe His Ser Ser
           355

<210> SEQ ID NO 4
<211> LENGTH: 352
<212> TYPE: PRT
<213> ORGANISM: Homo sapiens

<400> SEQUENCE: 4

Met Glu Gly Ile Ser Ile Tyr Thr Ser Asp Asn Tyr Thr Glu Glu Met
 1               5                  10                  15

Gly Ser Gly Asp Tyr Asp Ser Met Lys Glu Pro Cys Phe Arg Glu Glu

```
                    20                  25                  30
Asn Ala Asn Phe Asn Lys Ile Phe Leu Pro Thr Ile Tyr Ser Ile Ile
            35                  40                  45

Phe Leu Thr Gly Ile Val Gly Asn Gly Leu Val Ile Leu Val Met Gly
        50                  55                  60

Tyr Gln Lys Lys Leu Arg Ser Met Thr Asp Lys Tyr Arg Leu His Leu
65                  70                  75                  80

Ser Val Ala Asp Leu Phe Val Ile Thr Leu Pro Phe Trp Ala Val
                85                  90                  95

Asp Ala Val Ala Asn Trp Tyr Phe Gly Asn Phe Leu Cys Lys Ala Val
                100                 105                 110

His Val Ile Tyr Thr Val Asn Leu Tyr Ser Ser Val Leu Ile Leu Ala
            115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Phe Gln Phe Gln His Ile Met Val Gly Leu
        195                 200                 205

Ile Leu Pro Gly Ile Val Ile Leu Ser Cys Tyr Cys Ile Ile Ile Ser
    210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
        275                 280                 285

Ala Leu Ala Phe Phe His Cys Cys Leu Asn Pro Ile Leu Tyr Ala Phe
    290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350

<210> SEQ ID NO 5
<211> LENGTH: 355
<212> TYPE: PRT
<213> ORGANISM: Homo sapiens

<400> SEQUENCE: 5

Met Glu Thr Pro Asn Thr Thr Glu Asp Tyr Asp Thr Thr Thr Glu Phe
1               5                   10                  15

Asp Tyr Gly Asp Ala Thr Pro Cys Gln Lys Val Asn Glu Arg Ala Phe
                20                  25                  30

Gly Ala Gln Leu Leu Pro Pro Leu Tyr Ser Leu Val Phe Val Ile Gly
            35                  40                  45
```

-continued

```
Leu Val Gly Asn Ile Leu Val Leu Val Leu Val Gln Tyr Lys Arg
 50                  55                  60

Leu Lys Asn Met Thr Ser Ile Tyr Leu Leu Asn Leu Ala Ile Ser Asp
 65                  70                  75                  80

Leu Leu Phe Leu Phe Thr Leu Pro Phe Trp Ile Asp Tyr Lys Leu Lys
                 85                  90                  95

Asp Asp Trp Val Phe Gly Asp Ala Met Cys Lys Ile Leu Ser Gly Phe
            100                 105                 110

Tyr Tyr Thr Gly Leu Tyr Ser Glu Ile Phe Phe Ile Ile Leu Leu Thr
        115                 120                 125

Ile Asp Arg Tyr Leu Ala Ile Val His Ala Val Phe Ala Leu Arg Ala
    130                 135                 140

Arg Thr Val Thr Phe Gly Val Ile Thr Ser Ile Ile Trp Ala Leu
145                 150                 155                 160

Ala Ile Leu Ala Ser Met Pro Gly Leu Tyr Phe Ser Lys Thr Gln Trp
                165                 170                 175

Glu Phe Thr His His Thr Cys Ser Leu His Phe Pro His Glu Ser Leu
            180                 185                 190

Arg Glu Trp Lys Leu Phe Gln Ala Leu Lys Leu Asn Leu Phe Gly Leu
        195                 200                 205

Val Leu Pro Leu Leu Val Met Ile Ile Cys Tyr Thr Gly Ile Ile Lys
    210                 215                 220

Ile Leu Leu Arg Arg Pro Asn Glu Lys Lys Ser Lys Ala Val Arg Leu
225                 230                 235                 240

Ile Phe Val Ile Met Ile Ile Phe Phe Leu Phe Trp Thr Pro Tyr Asn
                245                 250                 255

Leu Thr Ile Leu Ile Ser Val Phe Gln Asp Phe Leu Phe Thr His Glu
            260                 265                 270

Cys Glu Gln Ser Arg His Leu Asp Leu Ala Val Gln Val Thr Glu Val
        275                 280                 285

Ile Ala Tyr Thr His Cys Cys Val Asn Pro Val Ile Tyr Ala Phe Val
    290                 295                 300

Gly Glu Arg Phe Arg Lys Tyr Leu Arg Gln Leu Phe His Arg Arg Val
305                 310                 315                 320

Ala Val His Leu Val Lys Trp Leu Pro Phe Leu Ser Val Asp Arg Leu
                325                 330                 335

Glu Arg Val Ser Ser Thr Ser Pro Ser Thr Gly Glu His Glu Leu Ser
            340                 345                 350

Ala Gly Phe
        355

<210> SEQ ID NO 6
<211> LENGTH: 374
<212> TYPE: PRT
<213> ORGANISM: Homo sapiens

<400> SEQUENCE: 6

Met Leu Ser Thr Ser Arg Ser Arg Phe Ile Arg Asn Thr Asn Glu Ser
 1                   5                  10                  15

Gly Glu Glu Val Thr Thr Phe Phe Asp Tyr Asp Tyr Gly Ala Pro Cys
                 20                  25                  30

His Lys Phe Asp Val Lys Gln Ile Gly Ala Gln Leu Leu Pro Pro Leu
             35                  40                  45

Tyr Ser Leu Val Phe Ile Phe Gly Phe Val Gly Asn Met Leu Val Val
 50                  55                  60
```

```
Leu Ile Leu Ile Asn Cys Lys Lys Leu Lys Cys Leu Thr Asp Ile Tyr
65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
        115                 120                 125

Phe Phe Ile Ile Leu Leu Thr Ile Asp Arg Tyr Leu Ala Ile Val His
    130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
            180                 185                 190

Tyr Phe Pro Arg Gly Trp Asn Asn Phe His Thr Ile Met Arg Asn Ile
        195                 200                 205

Leu Gly Leu Val Leu Pro Leu Leu Ile Met Val Ile Cys Tyr Ser Gly
    210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
                245                 250                 255

Thr Pro Tyr Asn Ile Val Ile Leu Leu Asn Thr Phe Gln Glu Phe Phe
            260                 265                 270

Gly Leu Ser Asn Cys Glu Ser Thr Ser Gln Leu Asp Gln Ala Thr Gln
        275                 280                 285

Val Thr Glu Thr Leu Gly Met Thr His Cys Cys Ile Asn Pro Ile Ile
    290                 295                 300

Tyr Ala Phe Val Gly Glu Lys Phe Arg Ser Leu Phe His Ile Ala Leu
305                 310                 315                 320

Gly Cys Arg Ile Ala Pro Leu Gln Lys Pro Val Cys Gly Gly Pro Gly
                325                 330                 335

Val Arg Pro Gly Lys Asn Val Lys Val Thr Thr Gln Gly Leu Leu Asp
            340                 345                 350

Gly Arg Gly Lys Gly Lys Ser Ile Gly Arg Ala Pro Glu Ala Ser Leu
        355                 360                 365

Gln Asp Lys Glu Gly Ala
    370

<210> SEQ ID NO 7
<211> LENGTH: 360
<212> TYPE: PRT
<213> ORGANISM: Homo sapiens

<400> SEQUENCE: 7

Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
                20                  25                  30

His Lys Phe Asp Val Lys Gln Ile Gly Ala Gln Leu Leu Pro Pro Leu
            35                  40                  45

Tyr Ser Leu Val Phe Ile Phe Gly Phe Val Gly Asn Met Leu Val Val
```

```
                    50                  55                  60
Leu Ile Leu Ile Asn Cys Lys Lys Leu Lys Cys Leu Thr Asp Ile Tyr
 65                  70                  75                  80

Leu Leu Asn Leu Ala Ile Ser Asp Leu Leu Phe Leu Ile Thr Leu Pro
                     85                  90                  95

Leu Trp Ala His Ser Ala Ala Asn Glu Trp Val Phe Gly Asn Ala Met
                    100                 105                 110

Cys Lys Leu Phe Thr Gly Leu Tyr His Ile Gly Tyr Phe Gly Gly Ile
                    115                 120                 125

Phe Phe Ile Ile Leu Leu Thr Ile Asp Arg Tyr Leu Ala Ile Val His
                    130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                    165                 170                 175

Ile Phe Thr Lys Cys Gln Lys Glu Asp Ser Val Tyr Val Cys Gly Pro
                    180                 185                 190

Tyr Phe Pro Arg Gly Trp Asn Asn Phe His Thr Ile Met Arg Asn Ile
                    195                 200                 205

Leu Gly Leu Val Leu Pro Leu Leu Ile Met Val Ile Cys Tyr Ser Gly
                    210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
                    245                 250                 255

Thr Pro Tyr Asn Ile Val Ile Leu Leu Asn Thr Phe Gln Glu Phe Phe
                    260                 265                 270

Gly Leu Ser Asn Cys Glu Ser Thr Ser Gln Leu Asp Gln Ala Thr Gln
                    275                 280                 285

Val Thr Glu Thr Leu Gly Met Thr His Cys Cys Ile Asn Pro Ile Ile
                    290                 295                 300

Tyr Ala Phe Val Gly Glu Lys Phe Arg Arg Tyr Leu Ser Val Phe Phe
305                 310                 315                 320

Arg Lys His Ile Thr Lys Arg Phe Cys Lys Gln Cys Pro Val Phe Tyr
                    325                 330                 335

Arg Glu Thr Val Asp Gly Val Thr Ser Thr Asn Thr Pro Ser Thr Gly
                    340                 345                 350

Glu Gln Glu Val Ser Ala Gly Leu
                    355                 360

<210> SEQ ID NO 8
<211> LENGTH: 355
<212> TYPE: PRT
<213> ORGANISM: Homo sapiens

<400> SEQUENCE: 8

Met Thr Thr Ser Leu Asp Thr Val Glu Thr Phe Gly Thr Thr Ser Tyr
 1               5                  10                  15

Tyr Asp Asp Val Gly Leu Leu Cys Glu Lys Ala Asp Thr Arg Ala Leu
                20                  25                  30

Met Ala Gln Phe Val Pro Pro Leu Tyr Ser Leu Val Phe Thr Val Gly
                35                  40                  45

Leu Leu Gly Asn Val Val Val Val Met Ile Leu Ile Lys Tyr Arg Arg
 50                 55                  60
```

```
Leu Arg Ile Met Thr Asn Ile Tyr Leu Leu Asn Leu Ala Ile Ser Asp
 65                  70                  75                  80

Leu Leu Phe Leu Val Thr Leu Pro Phe Trp Ile His Tyr Val Arg Gly
                 85                  90                  95

His Asn Trp Val Phe Gly His Gly Met Cys Lys Leu Leu Ser Gly Phe
            100                 105                 110

Tyr His Thr Gly Leu Tyr Ser Glu Ile Phe Phe Ile Ile Leu Leu Thr
        115                 120                 125

Ile Asp Arg Tyr Leu Ala Ile Val His Ala Val Phe Ala Leu Arg Ala
    130                 135                 140

Arg Thr Val Thr Phe Gly Val Ile Thr Ser Ile Val Thr Trp Gly Leu
145                 150                 155                 160

Ala Val Leu Ala Ala Leu Pro Glu Phe Ile Phe Tyr Glu Thr Glu Glu
                165                 170                 175

Leu Phe Glu Glu Thr Leu Cys Ser Ala Leu Tyr Pro Glu Asp Thr Val
            180                 185                 190

Tyr Ser Trp Arg His Phe His Thr Leu Arg Met Thr Ile Phe Cys Leu
        195                 200                 205

Val Leu Pro Leu Leu Val Met Ala Ile Cys Tyr Thr Gly Ile Ile Lys
    210                 215                 220

Thr Leu Leu Arg Cys Pro Ser Lys Lys Lys Tyr Lys Ala Ile Arg Leu
225                 230                 235                 240

Ile Phe Val Ile Met Ala Val Phe Phe Ile Phe Trp Thr Pro Tyr Asn
                245                 250                 255

Val Ala Ile Leu Leu Ser Ser Tyr Gln Ser Ile Leu Phe Gly Asn Asp
            260                 265                 270

Cys Glu Arg Ser Lys His Leu Asp Leu Val Met Leu Val Thr Glu Val
        275                 280                 285

Ile Ala Tyr Ser His Cys Cys Met Asn Pro Val Ile Tyr Ala Phe Val
    290                 295                 300

Gly Glu Arg Phe Arg Lys Tyr Leu Arg His Phe Phe His Arg His Leu
305                 310                 315                 320

Leu Met His Leu Gly Arg Tyr Ile Pro Phe Leu Pro Ser Glu Lys Leu
                325                 330                 335

Glu Arg Thr Ser Ser Val Ser Pro Ser Thr Ala Glu Pro Glu Leu Ser
            340                 345                 350

Ile Val Phe
        355

<210> SEQ ID NO 9
<211> LENGTH: 360
<212> TYPE: PRT
<213> ORGANISM: Homo sapiens

<400> SEQUENCE: 9

Met Asn Pro Thr Asp Ile Ala Asp Thr Thr Leu Asp Glu Ser Ile Tyr
  1               5                  10                  15

Ser Asn Tyr Tyr Leu Tyr Glu Ser Ile Pro Lys Pro Cys Thr Lys Glu
                 20                  25                  30

Gly Ile Lys Ala Phe Gly Glu Leu Phe Leu Pro Pro Leu Tyr Ser Leu
             35                  40                  45

Val Phe Val Phe Gly Leu Leu Gly Asn Ser Val Val Val Leu Val Leu
         50                  55                  60

Phe Lys Tyr Lys Arg Leu Arg Ser Met Thr Asp Val Tyr Leu Leu Asn
 65                  70                  75                  80
```

```
Leu Ala Ile Ser Asp Leu Leu Phe Val Phe Ser Leu Pro Phe Trp Gly
                85                  90                  95

Tyr Tyr Ala Ala Asp Gln Trp Val Phe Gly Leu Gly Leu Cys Lys Met
            100                 105                 110

Ile Ser Trp Met Tyr Leu Val Gly Phe Tyr Ser Gly Ile Phe Phe Val
            115                 120                 125

Met Leu Met Ser Ile Asp Arg Tyr Leu Ala Ile Val His Ala Val Phe
            130                 135                 140

Ser Leu Arg Ala Arg Thr Leu Thr Tyr Gly Val Ile Thr Ser Leu Ala
145                 150                 155                 160

Thr Trp Ser Val Ala Val Phe Ala Ser Leu Pro Gly Phe Leu Phe Ser
                165                 170                 175

Thr Cys Tyr Thr Glu Arg Asn His Thr Tyr Cys Lys Thr Lys Tyr Ser
            180                 185                 190

Leu Asn Ser Thr Thr Trp Lys Val Leu Ser Ser Leu Glu Ile Asn Ile
            195                 200                 205

Leu Gly Leu Val Ile Pro Leu Gly Ile Met Leu Phe Cys Tyr Ser Met
210                 215                 220

Ile Ile Arg Thr Leu Gln His Cys Lys Asn Glu Lys Lys Asn Lys Ala
225                 230                 235                 240

Val Lys Met Ile Phe Ala Val Val Val Leu Phe Leu Gly Phe Trp Thr
                245                 250                 255

Pro Tyr Asn Ile Val Leu Phe Leu Glu Thr Leu Val Glu Leu Glu Val
            260                 265                 270

Leu Gln Asp Cys Thr Phe Glu Arg Tyr Leu Asp Tyr Ala Ile Gln Ala
            275                 280                 285

Thr Glu Thr Leu Ala Phe Val His Cys Cys Leu Asn Pro Ile Ile Tyr
            290                 295                 300

Phe Phe Leu Gly Glu Lys Phe Arg Lys Tyr Ile Leu Gln Leu Phe Lys
305                 310                 315                 320

Thr Cys Arg Gly Leu Phe Val Leu Cys Gln Tyr Cys Gly Leu Leu Gln
                325                 330                 335

Ile Tyr Ser Ala Asp Thr Pro Ser Ser Ser Tyr Thr Gln Ser Thr Met
            340                 345                 350

Asp His Asp Leu His Asp Ala Leu
            355                 360

<210> SEQ ID NO 10
<211> LENGTH: 355
<212> TYPE: PRT
<213> ORGANISM: Homo sapiens

<400> SEQUENCE: 10

Met Asp Tyr Thr Leu Asp Leu Ser Val Thr Thr Val Thr Asp Tyr Tyr
1               5                   10                  15

Tyr Pro Asp Ile Phe Ser Ser Pro Cys Asp Ala Glu Leu Ile Gln Thr
            20                  25                  30

Asn Gly Lys Leu Leu Leu Ala Val Phe Tyr Cys Leu Leu Phe Val Phe
        35                  40                  45

Ser Leu Leu Gly Asn Ser Leu Val Ile Leu Val Leu Val Val Cys Lys
        50                  55                  60

Lys Leu Arg Ser Ile Thr Asp Val Tyr Leu Leu Asn Leu Ala Leu Ser
65                  70                  75                  80

Asp Leu Leu Phe Val Phe Ser Phe Pro Phe Gln Thr Tyr Tyr Leu Leu
```

-continued

```
                    85                  90                  95
Asp Gln Trp Val Phe Gly Thr Val Met Cys Lys Val Val Ser Gly Phe
                100                 105                 110

Tyr Tyr Ile Gly Phe Tyr Ser Ser Met Phe Phe Ile Thr Leu Met Ser
            115                 120                 125

Val Asp Arg Tyr Leu Ala Val Val His Ala Val Tyr Ala Leu Lys Val
        130                 135                 140

Arg Thr Ile Arg Met Gly Thr Thr Leu Cys Leu Ala Val Trp Leu Thr
145                 150                 155                 160

Ala Ile Met Ala Thr Ile Pro Leu Leu Val Phe Tyr Gln Val Ala Ser
                165                 170                 175

Glu Asp Gly Val Leu Gln Cys Tyr Ser Phe Tyr Asn Gln Gln Thr Leu
            180                 185                 190

Lys Trp Lys Ile Phe Thr Asn Phe Lys Met Asn Ile Leu Gly Leu Leu
        195                 200                 205

Ile Pro Phe Thr Ile Phe Met Phe Cys Tyr Ile Lys Ile Leu His Gln
    210                 215                 220

Leu Lys Arg Cys Gln Asn His Asn Lys Thr Lys Ala Ile Arg Leu Val
225                 230                 235                 240

Leu Ile Val Val Ile Ala Ser Leu Leu Phe Trp Val Pro Phe Asn Val
                245                 250                 255

Val Leu Phe Leu Thr Ser Leu His Ser Met His Ile Leu Asp Gly Cys
            260                 265                 270

Ser Ile Ser Gln Gln Leu Thr Tyr Ala Thr His Val Thr Glu Ile Ile
        275                 280                 285

Ser Phe Thr His Cys Cys Val Asn Pro Val Ile Tyr Ala Phe Val Gly
    290                 295                 300

Glu Lys Phe Lys Lys His Leu Ser Glu Ile Phe Gln Lys Ser Cys Ser
305                 310                 315                 320

Gln Ile Phe Asn Tyr Leu Gly Arg Gln Met Pro Arg Glu Ser Cys Glu
                325                 330                 335

Lys Ser Ser Cys Gln Gln His Ser Ser Arg Ser Ser Ser Val Asp
            340                 345                 350

Tyr Ile Leu
        355

<210> SEQ ID NO 11
<211> LENGTH: 350
<212> TYPE: PRT
<213> ORGANISM: Homo sapiens

<400> SEQUENCE: 11

Met Ser Asn Ile Thr Asp Pro Gln Met Trp Asp Phe Asp Asp Leu Asn
1               5                   10                  15

Phe Thr Gly Met Pro Pro Ala Asp Glu Asp Tyr Ser Pro Cys Met Leu
                20                  25                  30

Glu Thr Glu Thr Leu Asn Lys Tyr Val Val Ile Ile Ala Tyr Ala Leu
            35                  40                  45

Val Phe Leu Leu Ser Leu Leu Gly Asn Ser Leu Val Met Leu Val Ile
        50                  55                  60

Leu Tyr Ser Arg Val Gly Arg Ser Val Thr Asp Val Tyr Leu Leu Asn
65                  70                  75                  80

Leu Ala Leu Ala Asp Leu Leu Phe Ala Leu Thr Leu Pro Ile Trp Ala
                85                  90                  95
```

```
Ala Ser Lys Val Asn Gly Trp Ile Phe Gly Thr Phe Leu Cys Lys Val
            100                 105                 110
Val Ser Leu Leu Lys Glu Val Asn Phe Tyr Ser Gly Ile Leu Leu Leu
        115                 120                 125
Ala Cys Ile Ser Val Asp Arg Tyr Leu Ala Ile Val His Ala Thr Arg
    130                 135                 140
Thr Leu Thr Gln Lys Arg His Leu Val Lys Phe Val Cys Leu Gly Cys
145                 150                 155                 160
Trp Gly Leu Ser Met Asn Leu Ser Leu Pro Phe Phe Leu Phe Arg Gln
                165                 170                 175
Ala Tyr His Pro Asn Asn Ser Ser Pro Val Cys Tyr Glu Val Leu Gly
            180                 185                 190
Asn Asp Thr Ala Lys Trp Arg Met Val Leu Arg Ile Leu Pro His Thr
        195                 200                 205
Phe Gly Phe Ile Val Pro Leu Phe Val Met Leu Phe Cys Tyr Gly Phe
    210                 215                 220
Thr Leu Arg Thr Leu Phe Lys Ala His Met Gly Gln Lys His Arg Ala
225                 230                 235                 240
Met Arg Val Ile Phe Ala Val Val Leu Ile Phe Leu Leu Cys Trp Leu
                245                 250                 255
Pro Tyr Asn Leu Val Leu Leu Ala Asp Thr Leu Met Arg Thr Gln Val
            260                 265                 270
Ile Gln Glu Ser Cys Glu Arg Arg Asn Asn Ile Gly Arg Ala Leu Asp
        275                 280                 285
Ala Thr Glu Ile Leu Gly Phe Leu His Ser Cys Leu Asn Pro Ile Ile
    290                 295                 300
Tyr Ala Phe Ile Gly Gln Asn Phe Arg His Gly Phe Leu Lys Ile Leu
305                 310                 315                 320
Ala Met His Gly Leu Val Ser Lys Glu Phe Leu Ala Arg His Arg Val
                325                 330                 335
Thr Ser Tyr Thr Ser Ser Ser Val Asn Val Ser Ser Asn Leu
            340                 345                 350

<210> SEQ ID NO 12
<211> LENGTH: 360
<212> TYPE: PRT
<213> ORGANISM: Homo sapiens

<400> SEQUENCE: 12

Met Glu Asp Phe Asn Met Glu Ser Asp Ser Phe Glu Asp Phe Trp Lys
1               5                   10                  15
Gly Glu Asp Leu Ser Asn Tyr Ser Tyr Ser Ser Thr Leu Pro Pro Phe
            20                  25                  30
Leu Leu Asp Ala Ala Pro Cys Glu Pro Glu Ser Leu Glu Ile Asn Lys
        35                  40                  45
Tyr Phe Val Val Ile Ile Tyr Ala Leu Val Phe Leu Leu Ser Leu Leu
    50                  55                  60
Gly Asn Ser Leu Val Met Leu Val Ile Leu Tyr Ser Arg Val Gly Arg
65                  70                  75                  80
Ser Val Thr Asp Val Tyr Leu Leu Asn Leu Ala Leu Ala Asp Leu Leu
                85                  90                  95
Phe Ala Leu Thr Leu Pro Ile Trp Ala Ala Ser Lys Val Asn Gly Trp
            100                 105                 110
Ile Phe Gly Thr Phe Leu Cys Lys Val Val Ser Leu Leu Lys Glu Val
        115                 120                 125
```

```
Asn Phe Tyr Ser Gly Ile Leu Leu Ala Cys Ile Ser Val Asp Arg
    130                 135                 140

Tyr Leu Ala Ile Val His Ala Thr Arg Thr Leu Thr Gln Lys Arg Tyr
145                 150                 155                 160

Leu Val Lys Phe Ile Cys Leu Ser Ile Trp Gly Leu Ser Leu Leu Leu
                165                 170                 175

Ala Leu Pro Val Leu Leu Phe Arg Arg Thr Val Tyr Ser Ser Asn Val
            180                 185                 190

Ser Pro Ala Cys Tyr Glu Asp Met Gly Asn Asn Thr Ala Asn Trp Arg
        195                 200                 205

Met Leu Leu Arg Ile Leu Pro Gln Ser Phe Gly Phe Ile Val Pro Leu
    210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu Pro Tyr Asn Leu Val Leu Leu
            260                 265                 270

Ala Asp Thr Leu Met Arg Thr Gln Val Ile Gln Glu Thr Cys Glu Arg
        275                 280                 285

Arg Asn His Ile Asp Arg Ala Leu Asp Ala Thr Glu Ile Leu Gly Ile
    290                 295                 300

Leu His Ser Cys Leu Asn Pro Leu Ile Tyr Ala Phe Ile Gly Gln Lys
305                 310                 315                 320

Phe Arg His Gly Leu Leu Lys Ile Leu Ala Ile His Gly Leu Ile Ser
                325                 330                 335

Lys Asp Ser Leu Pro Lys Asp Ser Arg Pro Ser Phe Val Gly Ser Ser
            340                 345                 350

Ser Gly His Thr Ser Thr Thr Leu
        355                 360

<210> SEQ ID NO 13
<211> LENGTH: 368
<212> TYPE: PRT
<213> ORGANISM: Homo sapiens

<400> SEQUENCE: 13

Met Val Leu Glu Val Ser Asp His Gln Val Leu Asn Asp Ala Glu Val
1               5                   10                  15

Ala Ala Leu Leu Glu Asn Phe Ser Ser Ser Tyr Asp Tyr Gly Glu Asn
                20                  25                  30

Glu Ser Asp Ser Cys Cys Thr Ser Pro Pro Cys Pro Gln Asp Phe Ser
            35                  40                  45

Leu Asn Phe Asp Arg Ala Phe Leu Pro Ala Leu Tyr Ser Leu Leu Phe
        50                  55                  60

Leu Leu Gly Leu Leu Gly Asn Gly Ala Val Ala Ala Val Leu Leu Ser
65                  70                  75                  80

Arg Arg Thr Ala Leu Ser Ser Thr Asp Thr Phe Leu Leu His Leu Ala
                85                  90                  95

Val Ala Asp Thr Leu Leu Val Leu Thr Leu Pro Leu Trp Ala Val Asp
            100                 105                 110

Ala Ala Val Gln Trp Val Phe Gly Ser Gly Leu Cys Lys Val Ala Gly
        115                 120                 125

Ala Leu Phe Asn Ile Asn Phe Tyr Ala Gly Ala Leu Leu Leu Ala Cys
```

```
            130                 135                 140
Ile Ser Phe Asp Arg Tyr Leu Asn Ile Val His Ala Thr Gln Leu Tyr
145                 150                 155                 160

Arg Arg Gly Pro Pro Ala Arg Val Thr Leu Thr Cys Leu Ala Val Trp
                165                 170                 175

Gly Leu Cys Leu Leu Phe Ala Leu Pro Asp Phe Ile Phe Leu Ser Ala
            180                 185                 190

His His Asp Glu Arg Leu Asn Ala Thr His Cys Gln Tyr Asn Phe Pro
        195                 200                 205

Gln Val Gly Arg Thr Ala Leu Arg Val Leu Gln Leu Val Ala Gly Phe
    210                 215                 220

Leu Leu Pro Leu Leu Val Met Ala Tyr Cys Tyr Ala His Ile Leu Ala
225                 230                 235                 240

Val Leu Leu Val Ser Arg Gly Gln Arg Arg Leu Arg Ala Met Arg Leu
                245                 250                 255

Val Val Val Val Val Ala Phe Ala Leu Cys Trp Thr Pro Tyr His
            260                 265                 270

Leu Val Val Leu Val Asp Ile Leu Met Asp Leu Gly Ala Leu Ala Arg
        275                 280                 285

Asn Cys Gly Arg Glu Ser Arg Val Asp Val Ala Lys Ser Val Thr Ser
290                 295                 300

Gly Leu Gly Tyr Met His Cys Cys Leu Asn Pro Leu Leu Tyr Ala Phe
305                 310                 315                 320

Val Gly Val Lys Phe Arg Glu Arg Met Trp Met Leu Leu Leu Arg Leu
                325                 330                 335

Gly Cys Pro Asn Gln Arg Gly Leu Gln Arg Gln Pro Ser Ser Ser Arg
            340                 345                 350

Arg Asp Ser Ser Trp Ser Glu Thr Ser Glu Ala Ser Tyr Ser Gly Leu
        355                 360                 365

<210> SEQ ID NO 14
<211> LENGTH: 342
<212> TYPE: PRT
<213> ORGANISM: Homo sapiens

<400> SEQUENCE: 14

Met Ala Glu His Asp Tyr His Glu Asp Tyr Gly Phe Ser Ser Phe Asn
1               5                   10                  15

Asp Ser Ser Gln Glu Glu His Gln Asp Phe Leu Gln Phe Ser Lys Val
            20                  25                  30

Phe Leu Pro Cys Met Tyr Leu Val Val Phe Val Cys Gly Leu Val Gly
        35                  40                  45

Asn Ser Leu Val Leu Val Ile Ser Ile Phe Tyr His Lys Leu Gln Ser
    50                  55                  60

Leu Thr Asp Val Phe Leu Val Asn Leu Pro Leu Ala Asp Leu Val Phe
65                  70                  75                  80

Val Cys Thr Leu Pro Phe Trp Ala Tyr Ala Gly Ile His Glu Trp Val
                85                  90                  95

Phe Gly Gln Val Met Cys Lys Ser Leu Leu Gly Ile Tyr Thr Ile Asn
            100                 105                 110

Phe Tyr Thr Ser Met Leu Ile Leu Thr Cys Ile Thr Val Asp Arg Phe
        115                 120                 125

Ile Val Val Val Lys Ala Thr Lys Ala Tyr Asn Gln Gln Ala Lys Arg
    130                 135                 140
```

```
Met Thr Trp Gly Lys Val Thr Ser Leu Leu Ile Trp Val Ile Ser Leu
145                 150                 155                 160

Leu Val Ser Leu Pro Gln Ile Ile Tyr Gly Asn Val Phe Asn Leu Asp
                165                 170                 175

Lys Leu Ile Cys Gly Tyr His Asp Glu Ala Ile Ser Thr Val Val Leu
            180                 185                 190

Ala Thr Gln Met Thr Leu Gly Phe Phe Leu Pro Leu Leu Thr Met Ile
        195                 200                 205

Val Cys Tyr Ser Val Ile Ile Lys Thr Leu Leu His Ala Gly Gly Phe
    210                 215                 220

Gln Lys His Arg Ser Leu Lys Ile Ile Phe Leu Val Met Ala Val Phe
225                 230                 235                 240

Leu Leu Thr Gln Met Pro Phe Asn Leu Met Lys Phe Ile Arg Ser Thr
                245                 250                 255

His Trp Glu Tyr Tyr Ala Met Thr Ser Phe His Tyr Thr Ile Met Val
            260                 265                 270

Thr Glu Ala Ile Ala Tyr Leu Arg Ala Cys Leu Asn Pro Val Leu Tyr
        275                 280                 285

Ala Phe Val Ser Leu Lys Phe Arg Lys Asn Phe Trp Lys Leu Val Lys
    290                 295                 300

Asp Ile Gly Cys Leu Pro Tyr Leu Gly Val Ser His Gln Trp Lys Ser
305                 310                 315                 320

Ser Glu Asp Asn Ser Lys Thr Phe Ser Ala Ser His Asn Val Glu Ala
                325                 330                 335

Thr Ser Met Phe Gln Leu
            340

<210> SEQ ID NO 15
<211> LENGTH: 360
<212> TYPE: PRT
<213> ORGANISM: Homo sapiens

<400> SEQUENCE: 15

Met Asp Pro Glu Glu Thr Ser Val Tyr Leu Asp Tyr Tyr Tyr Ala Thr
1               5                   10                  15

Ser Pro Asn Ser Asp Ile Arg Glu Thr His Ser His Val Pro Tyr Thr
            20                  25                  30

Ser Val Phe Leu Pro Val Phe Tyr Thr Ala Val Phe Leu Thr Gly Val
        35                  40                  45

Leu Gly Asn Leu Val Leu Met Gly Ala Leu His Phe Lys Pro Gly Ser
    50                  55                  60

Arg Arg Leu Ile Asp Ile Phe Ile Ile Asn Leu Ala Ala Ser Asp Phe
65                  70                  75                  80

Ile Phe Leu Val Thr Leu Pro Leu Trp Val Asp Lys Glu Ala Ser Leu
                85                  90                  95

Gly Leu Trp Arg Thr Gly Ser Phe Leu Cys Lys Gly Ser Ser Tyr Met
            100                 105                 110

Ile Ser Val Asn Met His Cys Ser Val Leu Leu Leu Thr Cys Met Ser
        115                 120                 125

Val Asp Arg Tyr Leu Ala Ile Val Trp Pro Val Val Ser Arg Lys Phe
    130                 135                 140

Arg Arg Thr Asp Cys Ala Tyr Val Val Cys Ala Ser Ile Trp Phe Ile
145                 150                 155                 160

Ser Cys Leu Leu Gly Leu Pro Thr Leu Leu Ser Arg Glu Leu Thr Leu
                165                 170                 175
```

-continued

```
Ile Asp Asp Lys Pro Tyr Cys Ala Glu Lys Lys Ala Thr Pro Ile Lys
            180                 185                 190

Leu Ile Trp Ser Leu Val Ala Leu Ile Phe Thr Phe Val Pro Leu
        195                 200                 205

Leu Ser Ile Val Thr Cys Tyr Cys Cys Ile Ala Arg Lys Leu Cys Ala
        210                 215                 220

His Tyr Gln Gln Ser Gly Lys His Asn Lys Lys Leu Lys Lys Ser Ile
225                 230                 235                 240

Lys Ile Ile Phe Ile Val Ala Ala Phe Leu Val Ser Trp Leu Pro
                245                 250                 255

Phe Asn Thr Phe Lys Phe Leu Ala Ile Val Ser Gly Leu Arg Gln Glu
                260                 265                 270

His Tyr Leu Pro Ser Ala Ile Leu Gln Leu Gly Met Glu Val Ser Gly
            275                 280                 285

Pro Leu Ala Phe Ala Asn Ser Cys Val Asn Pro Phe Ile Tyr Tyr Ile
        290                 295                 300

Phe Asp Ser Tyr Ile Arg Arg Ala Ile Val His Cys Leu Cys Pro Cys
305                 310                 315                 320

Leu Lys Asn Tyr Asp Phe Gly Ser Ser Thr Glu Ser Asp Ser His
                325                 330                 335

Leu Thr Lys Ala Leu Ser Thr Phe Ile His Ala Glu Asp Phe Ala Arg
            340                 345                 350

Arg Arg Lys Arg Ser Val Ser Leu
            355                 360

<210> SEQ ID NO 16
<211> LENGTH: 380
<212> TYPE: PRT
<213> ORGANISM: Homo sapiens

<400> SEQUENCE: 16

Met Glu Glu Gly Gly Asp Phe Asp Asn Tyr Tyr Gly Ala Asp Asn Gln
1               5                   10                  15

Ser Glu Cys Glu Tyr Thr Asp Trp Lys Ser Ser Gly Ala Leu Ile Pro
                20                  25                  30

Ala Ile Tyr Met Leu Val Phe Leu Leu Gly Thr Thr Gly Asn Gly Leu
            35                  40                  45

Val Leu Trp Thr Val Phe Arg Ser Ser Arg Glu Lys Arg Arg Ser Ala
        50                  55                  60

Asp Ile Phe Ile Ala Ser Leu Ala Val Ala Asp Leu Thr Phe Val Val
65                  70                  75                  80

Thr Leu Pro Leu Trp Ala Thr Tyr Thr Tyr Arg Asp Tyr Asp Trp Pro
                85                  90                  95

Phe Gly Thr Phe Phe Cys Lys Leu Ser Ser Tyr Leu Ile Phe Val Asn
                100                 105                 110

Met Tyr Ala Ser Val Phe Cys Leu Thr Gly Leu Ser Phe Asp Arg Tyr
            115                 120                 125

Leu Ala Ile Val Arg Pro Val Ala Asn Ala Arg Leu Arg Leu Arg Val
        130                 135                 140

Ser Gly Ala Val Ala Thr Ala Val Leu Trp Val Leu Ala Ala Leu Leu
145                 150                 155                 160

Ala Met Pro Val Met Val Leu Arg Thr Gly Asp Leu Glu Asn Thr
                165                 170                 175

Thr Lys Val Gln Cys Tyr Met Asp Tyr Ser Met Val Ala Thr Val Ser
```

```
                180             185             190
Ser Glu Trp Ala Trp Glu Val Gly Leu Gly Val Ser Thr Thr Val
        195                 200                 205

Gly Phe Val Val Pro Phe Thr Ile Met Leu Thr Cys Tyr Phe Phe Ile
    210                 215                 220

Ala Gln Thr Ile Ala Gly His Phe Arg Lys Glu Arg Ile Glu Gly Leu
225                 230                 235                 240

Arg Lys Arg Arg Arg Leu Leu Ser Ile Ile Val Leu Val Val Thr
                245                 250                 255

Phe Ala Leu Cys Trp Met Pro Tyr His Leu Val Lys Thr Leu Tyr Met
            260                 265                 270

Leu Gly Ser Leu Leu His Trp Pro Cys Asp Phe Asp Leu Phe Leu Met
        275                 280                 285

Asn Ile Phe Pro Tyr Cys Thr Cys Ile Ser Tyr Val Asn Ser Cys Leu
    290                 295                 300

Asn Pro Phe Leu Tyr Ala Phe Phe Asp Pro Arg Phe Arg Gln Ala Cys
305                 310                 315                 320

Thr Ser Met Leu Cys Cys Gly Gln Ser Arg Cys Ala Gly Thr Ser His
                325                 330                 335

Ser Ser Ser Gly Glu Lys Ser Ala Ser Tyr Ser Ser Gly His Ser Gln
            340                 345                 350

Gly Pro Gly Pro Asn Met Gly Lys Gly Gly Glu Gln Met His Glu Lys
        355                 360                 365

Ser Ile Pro Tyr Ser Gln Glu Thr Leu Val Val Asp
    370                 375                 380

<210> SEQ ID NO 17
<211> LENGTH: 371
<212> TYPE: PRT
<213> ORGANISM: Homo sapiens

<400> SEQUENCE: 17

Met Glu Asp Glu Asp Tyr Asn Thr Ser Ile Ser Tyr Gly Asp Glu Tyr
1               5                   10                  15

Pro Asp Tyr Leu Asp Ser Ile Val Val Leu Glu Asp Leu Ser Pro Leu
                20                  25                  30

Glu Ala Arg Val Thr Arg Ile Phe Leu Val Val Val Tyr Ser Ile Val
            35                  40                  45

Cys Phe Leu Gly Ile Leu Gly Asn Gly Leu Val Ile Ile Ile Ala Thr
        50                  55                  60

Phe Lys Met Lys Lys Thr Val Asn Met Val Trp Phe Leu Asn Leu Ala
65                  70                  75                  80

Val Ala Asp Phe Leu Phe Asn Val Phe Leu Pro Ile His Ile Thr Tyr
                85                  90                  95

Ala Ala Met Asp Tyr His Trp Val Phe Gly Thr Ala Met Cys Lys Ile
            100                 105                 110

Ser Asn Phe Leu Leu Ile His Asn Met Phe Thr Ser Val Phe Leu Leu
        115                 120                 125

Thr Ile Ile Ser Ser Asp Arg Cys Ile Ser Val Leu Leu Pro Val Trp
130                 135                 140

Ser Gln Asn His Arg Ser Val Arg Leu Ala Tyr Met Ala Cys Met Val
145                 150                 155                 160

Ile Trp Val Leu Ala Phe Phe Leu Ser Ser Pro Ser Leu Val Phe Arg
                165                 170                 175
```

```
Asp Thr Ala Asn Leu His Gly Lys Ile Ser Cys Phe Asn Asn Phe Ser
            180                 185                 190

Leu Ser Thr Pro Gly Ser Ser Trp Pro Thr His Ser Gln Met Asp
        195                 200                 205

Pro Val Gly Tyr Ser Arg His Met Val Thr Val Thr Arg Phe Leu
    210                 215                 220

Cys Gly Phe Leu Val Pro Val Leu Ile Ile Thr Ala Cys Tyr Leu Thr
225                 230                 235                 240

Ile Val Cys Lys Leu Gln Arg Asn Arg Leu Ala Lys Thr Lys Lys Pro
                245                 250                 255

Phe Lys Ile Ile Val Thr Ile Ile Thr Phe Phe Leu Cys Trp Cys
                260                 265                 270

Pro Tyr His Thr Leu Asn Leu Leu Glu Leu His His Thr Ala Met Pro
        275                 280                 285

Gly Ser Val Phe Ser Leu Gly Leu Pro Leu Ala Thr Ala Leu Ala Ile
    290                 295                 300

Ala Asn Ser Cys Met Asn Pro Ile Leu Tyr Val Phe Met Gly Gln Asp
305                 310                 315                 320

Phe Lys Lys Phe Lys Val Ala Leu Phe Ser Arg Leu Val Asn Ala Leu
                325                 330                 335

Ser Glu Asp Thr Gly His Ser Ser Tyr Pro Ser His Arg Ser Phe Thr
                340                 345                 350

Lys Met Ser Ser Met Asn Glu Arg Thr Ser Met Asn Glu Arg Glu Thr
                355                 360                 365

Gly Met Leu
        370

<210> SEQ ID NO 18
<211> LENGTH: 355
<212> TYPE: PRT
<213> ORGANISM: Homo sapiens

<400> SEQUENCE: 18

Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Val Phe Gly Thr Val
            20                  25                  30

Phe Leu Ser Ile Phe Tyr Ser Val Ile Phe Ala Ile Gly Leu Val Gly
        35                  40                  45

Asn Leu Leu Val Val Phe Ala Leu Thr Asn Ser Lys Lys Pro Lys Ser
    50                  55                  60

Val Thr Asp Ile Tyr Leu Leu Asn Leu Ala Leu Ser Asp Leu Leu Phe
65                  70                  75                  80

Val Ala Thr Leu Pro Phe Trp Thr His Tyr Leu Ile Asn Glu Lys Gly
                85                  90                  95

Leu His Asn Ala Met Cys Lys Phe Thr Thr Ala Phe Phe Ile Gly
            100                 105                 110

Phe Phe Gly Ser Ile Phe Phe Ile Thr Val Ile Ser Ile Asp Arg Tyr
        115                 120                 125

Leu Ala Ile Val Leu Ala Ala Asn Ser Met Asn Asn Arg Thr Val Gln
    130                 135                 140

His Gly Val Thr Ile Ser Leu Gly Val Trp Ala Ala Ala Ile Leu Val
145                 150                 155                 160

Ala Ala Pro Gln Phe Met Phe Thr Lys Gln Lys Glu Asn Glu Cys Leu
                165                 170                 175
```

-continued

```
Gly Asp Tyr Pro Glu Val Leu Gln Glu Ile Trp Pro Val Leu Arg Asn
            180                 185                 190

Val Glu Thr Asn Phe Leu Gly Phe Leu Leu Pro Leu Leu Ile Met Ser
        195                 200                 205

Tyr Cys Tyr Phe Arg Ile Ile Gln Thr Leu Phe Ser Cys Lys Asn His
        210                 215                 220

Lys Lys Ala Lys Ala Ile Lys Leu Ile Leu Leu Val Val Ile Val Phe
225                 230                 235                 240

Phe Leu Phe Trp Thr Pro Tyr Asn Val Met Ile Phe Leu Glu Thr Leu
                245                 250                 255

Lys Leu Tyr Asp Phe Phe Pro Ser Cys Asp Met Arg Lys Asp Leu Arg
            260                 265                 270

Leu Ala Leu Ser Val Thr Glu Thr Val Ala Phe Ser His Cys Cys Leu
        275                 280                 285

Asn Pro Leu Ile Tyr Ala Phe Ala Gly Glu Lys Phe Arg Arg Tyr Leu
    290                 295                 300

Tyr His Leu Tyr Gly Lys Cys Leu Ala Val Leu Cys Gly Arg Ser Val
305                 310                 315                 320

His Val Asp Phe Ser Ser Ser Glu Ser Gln Arg Ser Arg His Gly Ser
                325                 330                 335

Val Leu Ser Ser Asn Phe Thr Tyr His Thr Ser Asp Gly Asp Ala Leu
            340                 345                 350

Leu Leu Leu
        355
```

MODIFIED ERYTHROCYTES AND USES THEREOF

TECHNICAL FIELD

The present invention relates to modified erythrocytes and methods of using the same for the treatment and prevention of viral infections.

BACKGROUND

Human immunodeficiency virus (HIV) infection is characterized as a systemic immunosuppressive disorder caused by the viral-mediated depletion of CD4 T cells or viral mediated loss of immune competence, which develops into the profound immunodeficiency that underlies the acquired immunodeficiency syndrome (AIDS). AIDS is characterized by various pathological conditions, including immune incompetence, opportunistic infections, neurological dysfunctions, and neoplastic growth.

Many drugs have been approved for the treatment of AIDS. Non-limiting examples of these drugs include nonnucleoside reverse transcriptase inhibitors, such as delavirdine (Rescriptor, Pfizer), Efavirenz (Sustiva, Bristol-Myers Squibb), and evirapine (Viramune, Boehringer Ingelheim); nucleoside reverse transcriptase inhibitors, such as Abacavir (Ziagen or ABC, GlaxoSmithKline), Didanosine (Videx or ddI, Bristol-Myers Squibb), Emtricitabine (Emtriva, Gilead Sciences), Lamivudine (Epivir, GlaxoSmithKline), Stavudine (Zerit, Bristol-Myers Squibb), Tenofovir DF (Viread, Gilead Sciences), Zalcitabine (Hivid, Hoffmnan-La Roche), Zidovudine (Retrovir or AZT, GlaxoSmithKline); protease inhibitors, such as Amprenavir (Agenerase, GlaxoSmithKline and Vertex Pharmaceuticals), Atazanavir (Reyataz, Bristol-Myers Squibb), Fosamprenavir (Lexiva, GlaxoSmithKline and Vertex Pharmaceuticals), Indinavir (Crixivan, Merck), Lopinavir (Kaletra, Abbott Laboratories), Nelfinavir (Viracept or NFV, Agouron Pharmaceuticals), Ritonavir (Norvir or RTV, Abbott Laboratories), Saquinavir (Fortovase, Hoffman-La Roche); and fusion inhibitors, such as Enfuvirtide (Fuzeon, Hoffman-La Roche and Trimeris).

The recommended treatment for HIV is a combination of three or more medications in a regimen called "highly active antiretroviral therapy" or "HAART." Exemplary HAART regimens include Sustiva+Epivir+(Retrovir, Viread or Zerit), Kaletra+Epivir+(Retrovir or Zerit), Sustiva+Emtriva+(Retrovir or Viread or Zerit), Kaletra+Emtriva+(Retrovir or Zerit), or Reyataz+(Epivir or Emtriva)+(Retrovir or Zerit). Introduction of HAART have led to a dramatic decline in both HIV-related illness and death. Early clinical trials demonstrated a reduction of plasma HIV RNA loads to undetectable levels in the majority of treated individuals. Subsequent studies, however, showed more limited success in achieving and maintaining viral suppression. Many patients experienced immunologic and clinical responses to HAART without sustained suppression of plasma viremia. Therefore, significant challenges still remain in the scientific and clinical battle against HIV and AIDS. In particular, there is a need for new methods that can effectively reduce plasma viremia in HIV-infected individuals.

SUMMARY OF THE INVENTION

The present invention addresses this need by providing modified erythrocytes which comprise HIV receptors capable of mediating HIV entry into the modified cells. These modified erythrocytes, when administered to an HIV patient, absorb and entrap plasma HIV, preventing the virus from infecting $CD4^+$ lymphocytes. The entrapped viral content is either degraded or deactivated within the erythrocytes, or is sequestered for the duration of entrapment and ultimately destroyed by erythrophagocytosis. The present invention also features modified erythrocytes which comprise receptor proteins for other viruses, and methods of using these erythrocytes for the treatment or prevention of other viral infections. In addition, the present invention features non-erythrocyte cells capable of capturing and internalizing viruses.

In one aspect, the present invention features a modified erythrocyte which comprises a recombinantly-produced receptor protein capable of binding to a virus. As used herein, "recombinantly produced" means that the receptor protein, or its coding sequence (including 5' or 3' regulatory regions), is prepared or modified using recombinant DNA technology.

In one embodiment, the recombinantly-produced receptor protein comprises an extracellular domain of a CD4 protein. As a non-limiting example, the recombinantly-produced receptor protein comprises or consists of a human CD4 protein.

In another embodiment, the recombinantly-produced receptor protein comprises an extracellular domain of an HIV coreceptor. Examples of HIV coreceptors suitable for the present invention include, but are not limited to, CXCR4, CCR5, CCR1, CCR2, CCR3, CCR4, CCR8, CXCR1, CXCR2, CXCR3, CXCR6, GPR15, APJ, CMKLR1, or CX3CR1. In a specific example, the recombinantly-produced receptor protein comprises or consists of an HIV coreceptor selected from CXCR4 or CCR5.

In still another embodiment, a modified erythrocyte of the present invention comprises CD4 and at least one HIV coreceptor, e.g., CXCR4, CCR5, CCR1, CCR2, CCR3, CCR4, CCR8, CXCR1, CXCR2, CXCR3, CXCR6, GPR15, APJ, CMKLR1, or CX3CR1. In one example, the modified erythrocyte comprises CD4 and an HIV coreceptor selected from CXCR4 or CCR5. In another example, the modified erythrocyte comprises CD4, CXCR4, and CCR5.

The modified erythrocytes of the present invention can be prepared from erythrocyte precursor cells, such as hematopoietic progenitor cells. Erythrocyte precursor cells can be isolated from peripheral blood, bone marrow, umbilical cord blood, or other suitable sources. Expression vectors encoding desired receptor proteins can be introduced into these precursor cells by transfection, transduction, electroporation, gene gun, or other gene transfer techniques. Alternatively, the endogenous genes that encode the desired receptor proteins can be modified to increase their transcription/translation activities. Precursor cells thus modified can be cultured under erythropoiesis conditions to generate terminally-differentiated, enucleated erythrocytes that express the desired receptor proteins.

The present invention also contemplates the use of other methods for preparing erythrocytes of the present invention. For instance, viral receptor proteins can be incorporated into mature enucleated erythrocytes through membrane fusion or other suitable means, as appreciated by those of ordinary skill in the art. As a non-limiting example, liposomes or micelles comprising desired viral receptor proteins (e.g., CD4, CXCR4, CCR5, or other HIV coreceptors) can be prepared using conventional techniques and then fused with mature enucleated erythrocytes. Mature enucleated erythrocytes thus modified can be administered to individuals in need thereof for the treatment or prevention of viral infections. Preferably, the donor of the mature erythrocytes is also the recipient of the modified cells.

In another aspect, the present invention features cell samples comprising modified erythrocytes of the present invention. A cell sample of the present invention can have a volume of from 10 to 1,000 ml, such as 50, 100, 200, 300, 400, 500, 600, 700, 800, or 900 ml. Each sample can include at least $1\times10^{10}$, $1\times10^{11}$, $1\times10^{12}$, $1\times10^{13}$, or more erythrocytes of the present invention.

In still another aspect, the present invention features methods for treating or preventing viral infections (e.g., HIV infections). These methods typically comprise administering a plurality of erythrocytes of the present invention to an individual in need thereof. In one example, the individual being treated has contracted HIV or is at risk of HIV contraction. The erythrocytes being administered comprise CD4 and at least one HIV coreceptor, such as CXCR4 or CCR5. Preferably, the erythrocytes being administered have the same ABO blood type as that of the recipient. More preferably, the erythrocytes are prepared from hematopoietic progenitor cells isolated from the recipient. In another example, the modified erythrocytes are prepared from mature enucleated erythrocytes isolated from the recipient. In many cases, the erythrocytes employed are modified with CD4 and HIV coreceptor(s) which are identical to the recipient's endogenous proteins.

The present invention further features the use of non-erythrocyte cells for the treatment or prevention of viral infections. The nuclei of these cells can be deactivated by radiation, chemical treatment, or other suitable means. These cells comprise the receptor protein(s) capable of mediating entry of a virus of interest into the cells. In one embodiment, the non-erythrocytes cells of the present invention are leukocytes which comprise CD4 and at least one HIV coreceptor (e.g., CXCR4 or CCR5). In many cases, the non-erythrocytes cells are modified with CD4 and HIV coreceptor(s) which are identical to the recipient's endogenous proteins.

Other features, objects, and advantages of the present invention are apparent in the detailed description that follows. It should be understood, however, that the detailed description, while indicating preferred embodiments of the invention, is given by way of illustration only, not limitation. Various changes and modifications within the scope of the invention will become apparent to those skilled in the art from the detailed description.

DETAILED DESCRIPTION

The present invention features modified erythrocytes which comprise receptor proteins for HIV or other viruses. These receptor proteins can mediate entry of the respective viruses into the modified cells, thereby removing the viruses from the blood or other tissues that are accessible by the erythrocytes. Because erythrocyte lacks nucleic acid synthesis machinery, an entrapped virus cannot replicate or otherwise initiate viral functions. As a result, the entrapped virus is either degraded or deactivated within the erythrocytes, or destroyed by phagocytes during erythrophagocytosis. Non-erythrocytes are also provided which can entrap the virus and prevent its use in cells which would otherwise serve the virus as a valid host cell, where the non-erythrocyte cannot serve as a host cell for the replication of the virus as caused by modifications to the cell as described herein.

The modified erythrocytes of the present invention can be prepared from hematopoietic progenitor cells transfected or transduced with exogenous genes that encode desired viral receptor proteins. Exemplary procedures suitable for this purpose are described in Malik et al., BLOOD, 91:2664-2671 (1998); Hanspal et al., BLOOD, 84:3494-3504 (1994); Wada et al., BLOOD, 75:505-511 (1990); and Fibach et al., BLOOD, 73:100-103 (1989), all of which are incorporated herein by reference in their entireties. In one example, hematopoietic progenitor cells are isolated from peripheral blood, bone marrow, or umbilical cord blood. These cells are typically CD34 positive and, therefore, can be purified using immunomagnetic beads coupled with anti-CD34 antibodies. The purified progenitor cells are transfected or transduced with expression vectors that encode viral receptor proteins, and then cultured under erythroid differentiation conditions (e.g., high concentrations of erythropoietin (EPO) and low concentrations of granulocyte-macrophage colony-stimulating factor (GM-CSF) and IL-3) to produce terminally-differentiated, enucleated erythrocytes that express the viral receptor proteins. Erythrocytes thus prepared are negative for DNA staining and therefore can be separated from other cells in the culture by using cell sorting techniques such as flow cytometers or fluorescence activated cell sorters.

In one aspect, the present invention features modified erythrocytes comprising HIV receptors. HIV is a member of the lentivirus family of retroviruses. There are two prevalent types of HIV, HIV-1 and HIV-2. Various strains having been identified for each type of HIV. HIV uses a receptor-mediated pathway in the infection of host cells. HIV-1 requires contact with two cell-surface receptors to gain entry into cells and initiate infection. CD4 is the primary receptor. CXCR4 and CCR5, members of the chemokine receptor family of proteins, serve as secondary coreceptors for HIV-1 strains that are tropic for T-cell lines or macrophages, respectively. Many HIV-2 strains also utilize CCR5 or CXCR4 to enter host cells.

CD4 (CD 4 antigen (p55)) is a cell-surface glycoprotein found on the mature helper T cells and immature thymocytes, as well as on monocytes and macrophages. Some cytotoxic T cells and natural killer cells also express CD4 protein. An exemplary human CD4 sequence is depicted in SEQ ID NO:1.

CCR5 (chemokine (C-C motif) receptor 5) is a member of the beta chemokine receptor family, which is predicted to have seven transmembrane domains similar to G protein-coupled receptors. This protein is expressed by T cells and macrophages, and is known to be a co-receptor for macrophage-tropic virus, including HIV, to enter host cells. Defective alleles of this gene have been associated with the HIV infection resistance. Expression of CCR5 was also detected in a promyeloblastic cell line. An exemplary human CCR5 sequence is illustrated in SEQ ID NO:2.

CXCR4 (chemokine (C-X-C motif) receptor 4; also known as fusin) is a CXC chemokine receptor specific for stromal cell-derived factor-1. CXCR4 also has seven transmembrane regions. It acts with the CD4 protein to support HIV entry into cells. Alternate transcriptional splice variants encoding different CXCR4 isoforms have been identified. Two exemplary CXCR4 isoforms are depicted in SEQ ID NOs: 3 and 4, respectively.

Without limiting the present invention to any particular theory, it is believed that the interaction between the viral envelope glycoprotein gp120 and CD4 triggers the fusion between viral and host membranes. This interaction, which is also facilitated by cell surface glycosaminoglycans, leads to conformational changes in gp120, which results in the interaction between gp120 and a secondary coreceptor, mostly CCR5 or CXCR4. The double engagement of CD4 and a secondary coreceptor induces a sharp conformational change of a second viral envelope protein, gp41, which acts as a fusogenic component leading to the fusion of viral and cell membranes required for the injection of the HIV ribonucleoprotein complex into the host cell cytoplasm.

It has been reported that HIV-1 strains transmitted in vivo generally use CCR5. These viruses typically infect macrophages and primary CD4+ lymphocytes, and do not form syncytia in vitro. These viruses are said to be macrophage tropic (M-tropic or R5 strain). After primary HIV-1 infection, viral populations are usually characterized by molecular heterogeneity.

Years after chronic infection is established, strains using CXCR4 emerge in about 50% of infected individuals. CXCR4 strains not only infect primary T lymphocytes but also replicate in T-cell lines and induce syncytia. These viruses are said to be T-cell tropic (T-tropic or X4 strain). This difference in cell tropism correlates with disease progression. During HIV infection, strains isolated from individuals early in the course of their infection are usually M-tropic, while viruses isolated from approximately 50% of individuals with advanced immunodeficiency also include viruses that are T-tropic. This suggests that the ability of the viral envelope to interact with CXCR4 represents an important feature in the pathogenesis of immunodeficiency and the development of full blown acquired immunodeficiency syndrome.

Other HIV coreceptors have also been reported. These coreceptors include, but are not limited to, CCR1, CCR2, CCR3, CCR4, CCR8, CXCR1, CXCR2, CXCR3, CXCR6, GPR15, APJ, CMKLR1, and CX3CR1. CCR1 (chemokine (C-C motif) receptor 1) is a member of the beta chemokine receptor family, which is predicted to have seven transmembrane domains. Chemokines and their receptors mediate signal transductions that are critical for the recruitment of effector immune cells to the site of inflammation. Knockout studies of the mouse CCR1 homolog suggested the roles of this gene in host protection from inflammatory response, and susceptibility to virus and parasite. The CCR1 gene and other chemokine receptor genes including CCR2, CCRL2, CCR3, CCR5 and CCXCR1 form a gene cluster on chromosome 3p. A non-limiting example of human CCR1 sequence is depicted in SEQ ID NO:5.

CCR2 (chemokine (C-C motif) receptor 2; also known as CCR2b) is a receptor for monocyte chemoattractant protein-1, a chemokine which specifically mediates monocyte chemotaxis. Monocyte chemoattractant protein-1 is involved in monocyte infiltration in inflammatory diseases such as rheumatoid arthritis as well as in the inflammatory response against tumors. CCR2 is capable of mediating agonist-dependent calcium mobilization and inhibition of adenylyl cyclase. At least two alternatively spliced CCR2 isoforms have been identified. Exemplary sequences for these two isoforms are depicted in SEQ ID NOs: 6 and 7, respectively.

CCR3 (chemokine (C-C motif) receptor 3) is receptor for C-C type chemokines. It belongs to family 1 of the G protein-coupled receptors. This receptor binds and responds to a variety of chemokines, including eotaxin (CCL11), eotaxin-3 (CCL26), MCP-3 (CCL7), MCP-4 (CCL13), and RANTES (CCL5). It is highly expressed in eosinophils and basophils, and is also detected in TH1 and TH2 cells, as well as in airway epithelial cells. This receptor may contribute to the accumulation and activation of eosinophils and other inflammatory cells in the allergic airway. At least two alternatively spliced transcript variants have been identified for CCR3. Both isoforms encode the same protein. An exemplary sequence for human CCR3 is depicted in SEQ ID NO:8.

CCR4 (chemokine (C-C motif) receptor 4) belongs to the G-protein-coupled receptor family. It is a receptor for the CC chemokine, including MIP-1, RANTES, TARC and MCP-1. CCR4 is expressed with high frequency in adult T-cell leukemia and human T-cell leukemia virus type 1-transformed T cells and in ATL skin lesions. An exemplary human CCR4 sequence is depicted in SEQ ID NO:9.

CCR8 (chemokine (C-C motif) receptor 8) is a member of the beta chemokine receptor family and predicted to have seven transmembrane domains. This receptor protein is preferentially expressed in the thymus. Studies of this receptor and its ligands suggested its role in regulation of monocyte chemotaxis and thymic cell apoptosis. This receptor may contribute to the proper positioning of activated T cells within the antigenic challenge sites and specialized areas of lymphoid tissues. An exemplary human CCR8 sequence is described in SEQ ID NO:10.

CXCR1 (interleukin 8 receptor, alpha; or IL8RA) is a member of the G-protein-coupled receptor family. This protein is a receptor for interleukin 8 (IL8). It binds to IL8 with high affinity, and transduces the signal through a G-protein activated second messenger system. Knockout studies in mice suggested that this protein inhibits embryonic oligodendrocyte precursor migration in developing spinal cord. An exemplary human CXCR1 sequence is illustrated in SEQ ID NO:11.

CXCR2 (interleukin 8 receptor, beta; or IL8RB) is also a member of the G-protein-coupled receptor family. Like CXCR1, this protein is a receptor for interleukin 8 (IL8). CXCR2 binds to chemokine (C-X-C motif) ligand 1 (CXCL1/MGSA), a protein with melanoma growth stimulating activity, and has been shown to be a major component required for serum-dependent melanoma cell growth. CXCR2 mediates neutrophil migration to sites of inflammation. The angiogenic effects of IL8 in intestinal microvascular endothelial cells are found to be mediated by CXCR2. Knockout studies in mice suggested that this receptor controls the positioning of oligodendrocyte precursors in developing spinal cord by arresting their migration. The genes encoding CXCR1 and CXCR2, as well as the IL8RBP gene, form a gene cluster in a region mapped to chromosome 2q33-q36. An exemplary human CXCR2 sequence is depicted in SEQ ID NO:12.

CXCR3 (chemokine (C-X-C motif) receptor 3) is a G protein-coupled receptor with selectivity for three chemokines—namely, IP10 (interferon-g-inducible 10 kDa protein), Mig (monokine induced by interferon-g), and I-TAC (interferon-inducible T cell a-chemoattractant). IP10, Mig and I-TAC belong to the structural subfamily of CXC chemokines, in which a single amino acid residue separates the first two of four highly conserved Cys residues. Binding of chemokines to CD183 induces cellular responses that are involved in leukocyte traffic, including integrin activation, cytoskeletal changes and chemotactic migration. Inhibition by *Bordetella pertussis* toxin suggests that heterotrimeric G protein of the Gi-subclass couple to CD183. A hallmark of CD183 is its prominent expression in vitro cultured effector/memory T cells, and in T cells present in many types of inflamed tissues. In addition, IP10, Mig and I-TAC are commonly produced by local cells in inflammatory lesion, suggesting that CD183 and its chemokines participate in the recruitment of inflammatory cells. An exemplary human CXCR3 sequence is provided in SEQ ID NO:13.

CXCR6 (chemokine (C-X-C motif) receptor 6; also known as STRL33) is predominantly localized in colorectal epithelial cells and some scattered stromal cells. It has been reported that HIV-2 isolates from aviremic and viremic individuals commonly use CCR5, GPR15, or CXCR6 as coreceptors, in combination with CD4. A non-limiting example of human CXCR6 sequence is depicted in SEQ ID NO:14.

GPR15 (G protein-coupled receptor 15; also know as BOB) plays a role in HIV gp120 binding to intestinal epithelial cells and gp120-induced cytopathic effects. An exemplary human GRP15 sequence is described in SEQ ID NO:15.

APJ (angiotensin II receptor-like 1 or AGTRL1) mediates effects of angiotensin II. This gene is related to the AGTR1 gene by sequence similarity. It was cloned based on a conserved transmembrane domain found in members of the G protein-coupled receptor gene family. An exemplary human APJ sequence is depicted in SEQ ID NO:16.

CMKLR1 (chemokine-like receptor 1; also known as ChemR23) has been reported to mediate the Resolvin E1 signal to attenuate nuclear factor-κB. A non-limiting example of human CMKLR1 sequence is depicted in SEQ ID NO:17.

CX3CR1 (chemokine (C-X3-C motif) receptor 1) is selectively expressed on various lineages of lymphocytes with high contents of intracellular perforin and granzyme B. The impact of CX3CR1 polymorphisms on HIV-1 pathogenesis and infection progression in children has been reported. A non-limiting example of human CX3CR1 sequence is described in SEQ ID NO:18.

The present invention features modified erythrocytes which comprise CD4 and at least one HIV coreceptor (e.g., 1, 2, 3, 4, 5, 6, 7, 8, 9, 10, or more coreceptors). Preferably, the CD4 or HIV coreceptor proteins employed in the present invention are human proteins (e.g., SEQ ID NOs:1-18). More preferably, the CD4 or HIV coreceptor proteins employed are identical to the corresponding endogenous proteins expressed in the individual being treated. The CD4 or HIV coreceptor proteins can also be modified to reduce or eliminate any potential graft-versus-host and host-versus-graft reactions including the use of endogenous proteins expressed in the individual being treated.

In one embodiment, a modified erythrocyte of the present invention comprises CD4 and at least one HIV coreceptor selected from the group consisting of CCR5, CXCR4, CCR1, CCR2, CCR3, CCR4, CCR8, CXCR1, CXCR2, CXCR3, CXCR6, GPR15, APJ, CMKLR1, and CX3CR1. In another embodiment, a modified erythrocyte of the present invention comprises CD4 and at least two different HIV coreceptors, each of which is selected from the group consisting of CCR5, CXCR4, CCR1, CCR2, CCR3, CCR4, CCR8, CXCR1, CXCR2, CXCR3, CXCR6, GPR15, APJ, CMKLR1, and CX3CR1. In still another embodiment, a modified erythrocyte of the present invention comprises CD4 and at least three different HIV coreceptors, each of which is selected from the group consisting of CCR5, CXCR4, CCR1, CCR2, CCR3, CCR4, CCR8, CXCR1, CXCR2, CXCR3, CXCR6, GPR15, APJ, CMKLR1, and CX3CR1.

In yet another embodiment, a modified erythrocyte of the present invention comprises CD4 and CCR5. The modified erythrocyte may further include one or more HIV coreceptors selected from CXCR4, CCR1, CCR2, CCR3, CCR4, CCR8, CXCR1, CXCR2, CXCR3, CXCR6, GPR15, APJ, CMKLR1, or CX3CR1.

In still yet another embodiment, a modified erythrocyte of the present invention comprises CD4 and CXCR4. The modified erythrocyte may further include one or more HIV coreceptors selected from CCR5, CCR1, CCR2, CCR3, CCR4, CCR8, CXCR1, CXCR2, CXCR3, CXCR6, GPR15, APJ, CMKLR1, or CX3CR1.

In a further embodiment, a modified erythrocyte of the present invention comprises CD4, CCR5, and CXCR4. The modified erythrocyte may further include one or more HIV coreceptors selected from CCR1, CCR2, CCR3, CCR4, CCR8, CXCR1, CXCR2, CXCR3, CXCR6, GPR15, APJ, CMKLR1, or CX3CR1.

In still another embodiment, a modified erythrocyte of the present invention comprises CD4, CCR5, CXCR4, CCR1, CCR2, CCR3, CCR4, CCR8, CXCR1, CXCR2, CXCR3, CXCR6, GPR15, APJ, CMKLR1, and CX3CR1.

The present invention also features modified erythrocytes which comprise one or more HIV coreceptors but not CD4. HIV-1 infection of CD4-negative cells in vitro has been reported. This infection, however, is usually much less efficient than infection of cells that express CD4. It has also been reported that CD4-negative brain astrocytes can be infected by HIV-1 in vivo, particularly in pediatric AIDS patients. This virus appears to utilize CXCR4 to infect CD4-negative cells. Substitution of the V3 loop of the viral gp120 protein with that of an HIV R5 strain can produce viruses capable of CD4-independent infection via CCR5. Certain HIV-2 isolates have also been reported to infect $CCR5^+$ or $CXCR4^+$ cells without CD4. The efficiency of CD4-independent infection by HIV-2 is often markedly higher than that of HIV-1. Therefore, modified erythrocytes comprising these HIV coreceptors, either in the presence or absence of CD4, can be used to capture and eliminate CD4-independent HIV strains.

In one embodiment, a modified erythrocyte of the present invention comprises CXCR4 but not CD4. The modified erythrocyte may further include one or more coreceptors selected from CCR5, CCR1, CCR2, CCR3, CCR4, CCR8, CXCR1, CXCR2, CXCR3, CXCR6, GPR15, APJ, CMKLR1, or CX3CR1.

In another embodiment, a modified erythrocyte of the present invention comprises CCR5 but not CD4. The modified erythrocyte may further include one or more coreceptors selected from CXCR4, CCR1, CCR2, CCR3, CCR4, CCR8, CXCR1, CXCR2, CXCR3, CXCR6, GPR15, APJ, CMKLR1, or CX3CR1.

In still another embodiment, a modified erythrocyte of the present invention comprises CXCR4 and CCR5 but not CD4. The modified erythrocyte may further include one or more coreceptors selected from CCR1, CCR2, CCR3, CCR4, CCR8, CXCR1, CXCR2, CXCR3, CXCR6, GPR15, APJ, CMKLR1, or CX3CR1

In yet another embodiment, a modified erythrocyte of the present invention comprises at least 1, 2, 3, 4, 5, 6, 7, 8, 9, 10, or more HIV coreceptors, each of which is selected from CXCR4, CCR5, CCR1, CCR2, CCR3, CCR4, CCR8, CXCR1, CXCR2, CXCR3, CXCR6, GPR15, APJ, CMKLR1, or CX3CR1.

The present invention further features modified erythrocytes which comprise CD4 but not other HIV coreceptors. These erythrocytes can compete against $CD4^+$ T cells or other cell types for the interaction with HIV virions, thereby reducing the chance of HIV infection of T cells or other cells.

The present invention contemplates the use of any combination of CD4 and/or HIV coreceptors for inclusion in a modified erythrocyte of the present invention. Non-limiting examples of coding sequences for these HIV receptor/coreceptor proteins are depicted in SEQ ID NOs:1-18.

In another aspect, the present invention features the use of functional equivalents of naturally-occurring HIV receptor/coreceptor proteins. These functional equivalents retain their abilities to interact with their respective viral proteins (e.g., gp120), and are capable of mediating HIV entry into host cells. In one embodiment, a functional equivalent of an HIV receptor/coreceptor has the same extracellular domain(s) as the original protein but different transmembrane or intracellular domains. Methods suitable for preparing such a chimeric protein are well known in the art. Any HIV receptor/coreceptor described above can be so modified. The extracellular, transmembrane, or intracellular domains of a naturally-occurring HIV receptor/coreceptor can be determined by using protein structure prediction programs such as TMHMM, or based on the annotations of Entrez or other available databases.

In another embodiment, the functional equivalents are biologically-active variants of HIV receptor/coreceptor proteins. A "variant" is a polypeptide which differs from the original protein by one or more amino acid substitutions, deletions, insertions, or other modifications. These modifications do not significantly change the biological activity of the original protein (e.g., the activity to mediate entry of HIV into host cells). In many cases, a variant retains at least 10%, 20%, 30%, 40%, 50%, 60%, 70%, 80%, 90%, 95%, or 100% of the biological activity of original protein. The biological activity of a variant can also be higher than that of the original protein. A variant can be naturally-occurring, such as by allelic variation or polymorphism, or deliberately engineered.

The amino acid sequence of a variant is substantially identical to that of the original protein. In many embodiments, a variant shares at least 50%, 60%, 70%, 80%, 85%, 90%, 95%, 99%, or more global sequence identity or similarity with the original protein. Sequence identity or similarity can be determined using various methods known in the art, such as Basic Local Alignment Tool (BLAST), dot matrix analysis, or the dynamic programming method. In one example, the sequence identity or similarity is determined by using the Genetics Computer Group (GCG) programs GAP (Needleman-Wunsch algorithm). Default values assigned by the programs can be employed, e.g., the penalty for opening a gap in one of the sequences is 11 and for extending the gap is 8. Similar amino acids can be defined by the BLOSUM62 substitution matrix. The amino acid sequences of a variant and the original protein can be substantially identical in one or more regions, but divergent in other regions.

Any method known in the art may be used to prepare the biologically-active variants of HIV receptor/coreceptor proteins. For instance, a variant can be prepared from an original protein by adding, deleting, substituting or modifying at least 1, 2, 3, 4, 5, 6, 7, 8, 9, 10, or more amino acid residues without significantly altering the biological activity of the protein. The amino acid residue(s) being substituted can be conservative or non-conservative residue(s). Conservative amino acid substitutions may be introduced into a protein sequence without significantly changing the structure or biological activity of the protein. Conservative amino acid substitutions can be made on the basis of similarity in polarity, charge, solubility, hydrophobicity, hydrophilicity, or the amphipathic nature of the residues. For instance, conservative amino acid substitutions can be made among amino acids with basic side chains, such as lysine (Lys or K), arginine (Arg or R) and histidine (His or H); amino acids with acidic side chains, such as aspartic acid (Asp or D) and glutamic acid (Glu or E); amino acids with uncharged polar side chains, such as asparagine (Asn or N), glutamine (Gln or Q), serine (Ser or S), threonine (Thr or T), and tyrosine (Tyr or Y); or amino acids with nonpolar side chains, such as alanine (Ala or A), glycine (Gly or G), valine (Val or V), leucine (Leu or L), isoleucine (Ile or I), proline (Pro or P), phenylalanine (Phe or F), methionine (Met or M), tryptophan (Trp or W) or cysteine (Cys or C). Examples of commonly used amino acid substitutions are illustrated in Table 1.

TABLE 1

Example of Amino Acid Substitutions

| Original Residues | Exemplary Substitutions | More Conservative Substitutions |
|---|---|---|
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4 Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

Other desired amino acid modifications can also be introduced into an HIV receptor/coreceptor protein. For instance, amino acid modification(s) can be introduced to improve the stability of the protein.

The modified erythrocytes of the present invention can be prepared from erythrocyte precursor cells, such as $CD34^+$ hematopoietic progenitor cells. Exemplary procedures suitable for the isolation and culturing of erythrocyte precursor cells are described in Malik et al., BLOOD, 91:2664-2671 (1998); Hanspal et al., BLOOD, 84:3494-3504 (1994); Wada et al., BLOOD, 75:505-511 (1990); and Fibach et al., BLOOD, 73:100-103 (1989), all of which are incorporated herein by reference. Other methods known in the art can also be used.

Erythrocyte precursor cells can be isolated from peripheral blood, bone marrow, umbilical cord blood, or other suitable sources. Preferably, the donor of the precursor cells is also the recipient of the progeny cells. The precursor cells can also be isolated from donors who have the same blood type as the recipients of the progeny cells. These donors or recipients can be either infected with the virus being treated, or disease-free.

Expression vectors encoding desired HIV receptor/coreceptor proteins (e.g., CD4, CCR5, or CXCR4) can be introduced into erythrocyte precursor cells by transfection, transduction, electroporation, gene gun, or other gene transfer means. Vectors suitable for this purpose include, but are not limited to, viral vectors such as retroviral, lentiviral, adenoviral, adeno-associated viral (AAV), herpes viral, alphavirus, astrovirus, coronavirus, orthomyxovirus, papovavirus, paramyxovirus, parvovirus, picornavirus, poxvirus, or togavirus vectors. Liposomally-encapsulated expression vectors can also be used. An expression vector can be stably or transiently incorporated into the erythrocyte precursor cells. The cells are then cultured under appropriate conditions (e.g., in the presence of macrophages, or high concentrations of EPO in combination with low concentrations of GM-CSF and IL-3) to produce terminally-differentiated erythrocytes that express the desired HIV receptor/coreceptor proteins.

Selection of cells that are transfected or transduced with exogenous sequences is a matter of routine design within the level of ordinary skill in the art. In a non-limiting example, this is achieved by using selectable markers in the exogenous sequences. Markers suitable for this purpose include, but are not limited to, neomycin (G418), hygromycin, puromycin, zeocin, colchine, methotrexate, or methionine sulfoximine resistance genes.

For each expressed HIV receptor/coreceptor protein, an erythrocyte precursor cell can include one or more copies of the coding sequence for that protein. These copies can be carried by the same or different expression vectors. The coding sequences for different HIV receptor/coreceptor proteins can also be carried by the same or different expression vectors. In one example, an erythrocyte precursor cell of the present invention is transfected or transduced with an expression vector which encodes CD4 and an HIV coreceptor selected from CCR5, CXCR4, CCR1, CCR2, CCR3, CCR4, CCR8, CXCR1, CXCR2, CXCR3, CXCR6, GPR15, APJ, CMKLR1 or CX3CR1. In another example, an erythrocyte precursor cell of the present invention is transfected or transduced with an expression vector which encodes CD4 and at least two different HIV coreceptors selected from CCR5, CXCR4, CCR1, CCR2, CCR3, CCR4, CCR8, CXCR1, CXCR2, CXCR3, CXCR6, GPR15, APJ, CMKLR1 or CX3CR1. Any combination of these coreceptors is contemplated by the present invention. In still another example, an erythrocyte precursor cell of the present invention is transfected or transduced with an expression vector which encodes one or more HIV coreceptors but not CD4, where each of the HIV coreceptors is selected from CCR5, CXCR4, CCR1, CCR2, CCR3, CCR4, CCR8, CXCR1, CXCR2, CXCR3, CXCR6, GPR15, APJ, CMKLR1 or CX3 CR1.

The present invention further features the use of endogenous HIV receptor/coreceptor genes with modifications in their regulatory sequences. For instance, a viral promoter having high expression activity (e.g., CMV promoter) can be added to or substituted for the promoter of an endogenous HIV receptor/coreceptor gene. Methods suitable for this purpose include homologous recombination or other gene targeting techniques. The introduced viral promoter remains active during the culturing and differentiation of erythrocyte precursor cells, thereby allowing sufficient expression of the endogenous HIV receptor/coreceptor in the terminally-differentiated erythrocytes.

Terminally-differentiated, enucleated erythrocytes can be separated from other cells based on their DNA content. In a non-limiting example, cells are first labeled with a vital DNA dye, such as Hoechst 33342 (Invitrogen Corp.). Hoechst 33342 is a cell-permeant nuclear counterstain that emits blue fluorescence when bound to double-stranded DNA. Undifferentiated precursor cells, macrophages or other nucleated cells in the culture are stained by Hoechst 33342, while enucleated erythrocytes are Hoechst-negative. The Hoechst-positive cells can be separated from enucleated erythrocytes by using fluorescence activated cell sorters or other cell sorting techniques. The Hoechst dye can be removed from the isolated erythrocytes by dialysis or other suitable means.

Erythrocytes thus prepared can be centrifuged and resuspended in appropriate solution (e.g., standard AS-3 solution) for infusion into individuals in need thereof. Preferably, the erythrocytes to be infused have the same ABO type as that of the recipient to minimize the risk of infusion-associated immune reactions. The erythrocytes can also be pretreated to remove blood type-specific antigens or otherwise reduce antigenicities. Methods suitable for this purpose include, but are not limited to, those described in U.S. Patent Application Publication Nos. 20010006772 and 20030207247. In addition to infusion, the modified erythrocytes of the present invention can also be administered via other suitable routes, as appreciated by those of ordinary skill in the art.

The dosage and frequency of the administration can be determined by the attending physician based on various factors such as the severity of disease, the patient's age, sex and diet, the severity of any inflammation, time of administration, and other clinical factors. In one example, an intravenous administration is initiated at a dose which is minimally effective, and the dose is increased over a pre-selected time course until a positive effect is observed. Subsequently, incremental increases in dosage are made limiting to levels that produce a corresponding increase in effect while taking into account any adverse affects that may appear.

Non-limited examples of suitable dosages can range, for example, from $1 \times 10^{10}$ to $1 \times 10^{14}$, from $1 \times 10^{11}$ to $1 \times 10^{13}$, or from $5 \times 10^{11}$ to $5 \times 10^{12}$ erythrocytes of the present invention. Specific examples include about $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, or more erythrocytes of the present invention. Each dose of erythrocytes can be administered at intervals such as once daily, once weekly, twice weekly, once monthly, or twice monthly.

The expression level of each HIV receptor or coreceptor protein in the modified erythrocytes can also be adjusted to achieve optimal treatment effects. These can be accomplished by using promoters of different strengths to regulate the expression of the HIV receptor or coreceptor proteins.

Progress of a treatment can be monitored by periodic assessment of disease progression using methods known in the art. For instance, a positive effect can be determined by measuring reduction in viral load, either in plasma or cells (e.g., $CD4^+$ cells), increase in T cell or other cell counts (e.g., $CD3^+$, $CD4^+$, or $CD8^+$ cells), or improvement in T cell diversity. Preferably, the modified erythrocytes employed comprise HIV coreceptors that are recognizable or utilized by the HIV strain(s) in the patient being treated.

The modified erythrocytes of the present invention, when administered, bind to plasma HIV and induce the injection of the HIV ribonucleoprotein complex into the cells. Because terminally-differentiated erythrocytes lack nucleic acid synthesis machinery, the entrapped HIV RNA is incapable of being effectively reverse transcribed and is gradually degraded or deactivated within the cells. Any remaining activities of the entrapped HIV content can be eventually destroyed by erythrophagocytosis. In addition, enucleated cells lack nuclei and other machineries necessary for HIV to complete its replication cycle and ultimately manufacture proteins. With no means of replication and no means for escape, HIV components are entrapped in the enucleated cells. Even if the entrapped viral materials escape, these materials are incapable of binding to other cells to initial the fusion process and therefore are not infectious.

The modified erythrocytes of the present invention can be used alone or in combination with other anti-HIV drugs for the treatment or prevention of HIV infections. For instance, the modified erythrocytes of the present invention can be administered with one or more antiretroviral drugs selected from nonnucleoside reverse transcriptase inhibitors (such as delavirdine, Efavirenz, or evirapine); nucleoside reverse transcriptase inhibitors (such as Abacavir, Didanosine, Emtricitabine, Lamivudine, Stavudine, Tenofovir DF, Zalcitabine, or Zidovudine); protease inhibitors (such as Amprenavir, Atazanavir, Fosamprenavir, Indinavir, Lopinavir, Nelfinavir, Ritonavir, or Saquinavir); or fusion inhibitors (such as Enfuvirtide). The modified erythrocytes of the present invention can also be used in conjunction with a HAART regimen.

The above description focuses on modified erythrocytes comprising HIV receptor/coreceptor proteins and methods of using the same to treat or prevent HIV infections. As appreciated by one of ordinary skill in the art, the same methodology can be readily adapted to making modified erythrocytes that comprise receptors for other viruses. These receptors can mediate entry of the corresponding viruses into the modified erythrocytes, thereby preventing the viruses from infecting other cells. The captured virions or their components are degraded or deactivated within the erythrocytes as time elapses, or are eventually destroyed by erythrophagocytosis.

Viruses amenable to the present invention include, but are not limited to, those whose infection involves injection of genetic materials into host cells upon binding to cell surface receptors. Other viruses whose infection is mediated by cell surface receptors can also be treated according to the present invention. Non-limiting examples of these viruses can be selected from Paramyxoviridae (e.g., pneumovirus, morbillivirus, metapneumovirus, respirovirus or rubulavirus), Adenoviridae (e.g., adenovirus), Arenaviridae (e.g., arenavirus such as lymphocytic choriomeningitis virus), Arteriviridae (e.g., porcine respiratory and reproductive syndrome virus or equine arteritis virus), Bunyaviridae (e.g., phlebovirus or hantavirus), Caliciviridae (e.g., Norwalk virus), Coronaviridae (e.g., coronavirus or torovirus), Filoviridae (e.g., Ebola-like viruses), Flaviviridae (e.g., hepacivirus or flavivirus), Herpesviridae (e.g., simplexvirus, varicellovirus, cytomegalovirus, roseolovirus, or lymphocryptovirus), Orthomyxoviridae (e.g., influenza virus or thogotovirus), Parvoviridae (e.g., parvovirus), Picornaviridae (e.g., enterovirus or hepatovirus), Poxviridae (e.g., orthopoxvirus, avipoxvirus, or leporipoxvirus), Retroviridae (e.g., lentivirus or spumavirus), Reoviridae (e.g., rotavirus), Rhabdoviridae (e.g., lyssavirus, novirhabdovirus, or vesiculovirus), and Togaviridae (e.g., alphavirus or rubivirus). Specific examples of these viruses include human respiratory coronavirus, influenza viruses A-C, hepatitis viruses A to G, and herpes simplex viruses 1-9.

Preferably, a virus being treated circulates in the blood stream, and can be transmitted to a naive cell through interaction with receptor protein(s) on the cell surface. A modified erythrocyte expressing the receptor protein(s) can be administered to an individual who has contracted or is at risk of contraction of the virus, to reduce the plasma virus titer or the risk of infection. In addition, should the virus face a decreasing ability to access enough host cells per unit of time, this effect correlates with an inability of the virus to perpetuate the infection or perpetuate deleterious effect to the host in question. The viral infection can therefore be suppressed and contained.

The present invention further contemplates the use of other modified cells for the entrapment and elimination of viruses. Non-limiting examples of these cells included T cells, macrophages, neutrophils, natural killer cells, or other leukocytes. These cells can be prepared from hematopoietic progenitor cells or mature cells. Viral receptor proteins or sequences encoding the same can be introduced into hematopoietic progenitor cells or mature non-erythrocyte cells using the methods described above. Hematopoietic progenitor cells that are not modified with exogenous genes can also be employed, provided that the progeny cells derived therefrom comprise the desired endogenous viral receptors. The hematopoietic progenitor cells can be cultured under conditions to allow differentiation into desired cell types. The differentiated cells are then isolated and used for infusion into a patient in need thereof. In many embodiments, the nuclei of the differentiated cells are deactivated before use. Methods suitable for this purpose include radiation, chemical treatment, or other suitable means.

A modified cell of the present invention can also include agents capable of deactivating or destroying the entrapped viral content. Non-limiting examples of suitable agents include anti-viral drugs, proteases, nucleases, antisense molecules, ribozymes, RNAi molecules (e.g., siRNA or shRNA), or other molecules that are toxic or detrimental to the entrapped viral components. These agents can be introduced into a modified cell of the present invention by electroporation, microinjection, gene vectors or other suitable means, as appreciated by one of ordinary skill in the art.

The foregoing description of the present invention provides illustration and description, but is not intended to be exhaustive or to limit the invention to the precise one disclosed. Modifications and variations consistent with the above teachings may be acquired from practice of the invention. Thus, it is noted that the scope of the invention is defined by the claims and their equivalents.

What is claimed is:

1. An isolated erythrocyte comprising a recombinantly-produced receptor protein capable of binding to a virus, wherein said receptor protein comprises an extracellular domain of an HIV coreceptor.

2. The erythrocyte of claim 1, wherein said erythrocyte further comprises an extracellular domain of CD4.

3. The erythrocyte of claim 1, wherein said erythrocyte further comprises CD4.

4. An isolated erythrocyte comprising a recombinantly-produced receptor protein capable of binding to a virus, wherein said receptor protein comprises CD4, wherein said erythrocyte further comprises an HIV coreceptor selected from the group consisting of CXCR4, CCR5, CCR1, CCR2, CCR3, CCR4, CCR8, CXCR1, CXCR2, CXCR3, CXCR6, GPR15, APJ, CMKLR1, and CX3CR1.

5. An isolated erythrocyte comprising a recombinantly-produced receptor protein capable of binding to a virus, wherein said receptor protein comprises CD4, wherein said erythrocyte further comprises an HIV coreceptor selected from the group consisting of CXCR4 and CCR5.

6. An isolated erythrocyte comprising a recombinantly-produced receptor protein capable of binding to a virus, wherein said receptor protein comprises CD4, and wherein said erythrocyte further comprises CXCR4 and CCR5.

7. An isolated erythrocyte comprising a recombinantly-produced-receptor protein capable of binding to a virus, wherein said receptor is CD4 and said erythrocyte further comprises an HIV coreceptor, wherein said erythrocyte is an enucleated erythrocyte prepared from a human hematopoietic progenitor cell, and said hematopoietic progenitor comprises an exogenous sequence encoding said receptor protein.

8. A cell sample comprising at least $1 \times 10^{10}$ erythrocytes of claim 1.

9. A cell sample comprising at least $1 \times 10^{11}$ erythrocytes of claim 1.

10. A cell sample comprising at least $1 \times 10^{12}$ erythrocytes of claim 1.

11. A method for producing an erythrocyte comprising a recombinantly-produced receptor protein capable of binding to a virus, wherein said receptor is CD4 and said erythrocyte further comprises an HIV coreceptor, the method comprising the steps of:

isolating a hematopoietic progenitor cell from a subject;
introducing into the hematopoietic progenitor cell an expression vector which encodes said receptor protein and said receptor protein; and
differentiating the hematopoietic progenitor cell into enucleated erythrocytes.

12. An isolated erythrocyte comprising CD4 and at least one HIV coreceptor selected from CXCR4 and CCR5.

13. The isolated erythrocyte of claim 12, wherein each said HIV receptor or coreceptor protein is selected from the group consisting of CD4, CXCR4, and CCR5.

14. An isolated cell comprising a deactivated nucleus and a receptor protein capable of binding to a virus, wherein said cell is a leukocyte, and said receptor protein comprises CD4 or an HIV coreceptor.

15. The erythrocyte of claim 4, wherein said receptor protein comprises an extracellular domain of CD4.

16. The erythrocyte of claim 5, wherein said receptor protein comprises an extracellular domain of CD4.

17. The erythrocyte of claim 6, wherein said receptor protein comprises an extracellular domain of CD4.

18. The erythrocyte of claim 7, wherein said receptor protein comprises an extracellular domain of CD4.

19. The erythrocyte of claim 11, wherein said receptor protein comprises an extracellular domain of CD4.

20. The erythrocyte of claim 7, wherein said receptor protein comprises CD4.

21. The erythrocyte of claim 11, wherein said receptor protein comprises CD4.

22. A cell sample comprising at least $1 \times 10^{10}$ erythrocytes of claim 4.

23. A cell sample comprising at least $1 \times 10^{10}$ erythrocytes of claim 5.

24. A cell sample comprising at least $1 \times 10^{10}$ erythrocytes of claim 6.

25. A cell sample comprising at least $1 \times 10^{10}$ erythrocytes of claim 7.

26. A cell sample comprising at least $1 \times 10^{10}$ erythrocytes of claim 11.

27. A cell sample comprising at least $1 \times 10^{11}$ erythrocytes of claim 4.

28. A cell sample comprising at least $1 \times 10^{11}$ erythrocytes of claim 5.

29. A cell sample comprising at least $1 \times 10^{11}$ erythrocytes of claim 6.

30. A cell sample comprising at least $1 \times 10^{11}$ erythrocytes of claim 7.

31. A cell sample comprising at least $1 \times 10^{11}$ erythrocytes of claim 11.

32. A cell sample comprising at least $1 \times 10^{12}$ erythrocytes of claim 4.

33. A cell sample comprising at least $1 \times 10^{12}$ erythrocytes of claim 5.

34. A cell sample comprising at least $1 \times 10^{12}$ erythrocytes of claim 6.

35. A cell sample comprising at least $1 \times 10^{12}$ erythrocytes of claim 7.

36. A cell sample comprising at least $1 \times 10^{12}$ erythrocytes of claim 11.

* * * * *